United States Patent
Joh

(10) Patent No.: US 11,224,535 B2
(45) Date of Patent: Jan. 18, 2022

(54) WEARABLE URINARY COLLECTION APPARATUS

(71) Applicant: William Kyungha Joh, West Bloomfield, MI (US)

(72) Inventor: William Kyungha Joh, West Bloomfield, MI (US)

( * ) Notice: Subject to any disclaimer, the term of this patent is extended or adjusted under 35 U.S.C. 154(b) by 0 days.

(21) Appl. No.: 16/952,232

(22) Filed: Nov. 19, 2020

(65) Prior Publication Data

US 2021/0069007 A1    Mar. 11, 2021

Related U.S. Application Data

(63) Continuation-in-part of application No. 16/376,245, filed on Apr. 5, 2019, now abandoned.

(60) Provisional application No. 63/101,607, filed on May 8, 2020, provisional application No. 63/100,069, filed on Feb. 28, 2020, provisional application No. 62/765,200, filed on Aug. 20, 2018, provisional application No. 62/763,748, filed on Jul. 2, 2018, provisional application No. 62/763,239, filed on Jun. 6, 2018.

(51) Int. Cl.
*A61F 5/44*     (2006.01)
*A61F 5/453*    (2006.01)
*A61F 5/449*    (2006.01)
*A61F 5/455*    (2006.01)

(52) U.S. Cl.
CPC ............ *A61F 5/453* (2013.01); *A61F 5/4405* (2013.01); *A61F 5/449* (2013.01); *A61F 5/4556* (2013.01); *A61F 2005/4402* (2013.01)

(58) Field of Classification Search
CPC ........ A61F 5/453; A61F 5/4405; A61F 5/449; A61F 5/4556; A61F 2005/4402
USPC ........................................................ 604/350
See application file for complete search history.

(56) References Cited

U.S. PATENT DOCUMENTS

| 3,356,091 A | | 12/1967 | Patterson | |
|---|---|---|---|---|
| 3,374,939 A | * | 3/1968 | McMenimen | A61F 5/44 604/350 |
| 3,651,810 A | * | 3/1972 | Ormerod | A61F 5/453 604/329 |

(Continued)

FOREIGN PATENT DOCUMENTS

WO     2006/077351 A1    7/2006

*Primary Examiner* — Andrew J Mensh
(74) *Attorney, Agent, or Firm* — Carrier Blackman & Associates, P.C.; Joseph P. Carrier; William D. Blackman

(57) ABSTRACT

A wearable urinary collection apparatus for being worn by a user, including an elongate, watertight, flexible receptacle having an entrance opening near one end thereof and an elongate, flexible backflow inhibiting device which is connected to and extends within a portion of the flexible receptacle and also includes an entrance opening to receive the user's penis therein. At least one of the entrance opening of the receptacle and the entrance opening of the backflow inhibiting device is configured to receive the user's penis therein such that urine discharged from the penis flows through the backflow inhibiting device into the receptacle. The receptacle and the backflow inhibiting device are each formed of flexible plastic sheet material and are each configured to collapse flat when not in use, and the backflow inhibiting device has constrictions formed therein for constricting and diverting flow of urine therethrough.

11 Claims, 15 Drawing Sheets

(56) References Cited

U.S. PATENT DOCUMENTS

| | | | | |
|---|---|---|---|---|
| 4,533,354 A * | 8/1985 | Jensen | ............... | A61F 5/44 |
| | | | | 604/323 |
| 4,604,095 A * | 8/1986 | Samuelsen | ............ | A61F 5/4405 |
| | | | | 604/323 |
| 5,618,277 A * | 4/1997 | Goulter | ................ | A61F 5/4405 |
| | | | | 604/349 |
| 6,679,867 B2 * | 1/2004 | Miskie | ................. | A61F 5/453 |
| | | | | 604/323 |
| 7,087,043 B2 * | 8/2006 | Dolan | ................... | A61F 5/453 |
| | | | | 604/349 |
| 8,764,716 B2 * | 7/2014 | Christensen | ......... | A61F 5/4405 |
| | | | | 604/328 |
| 2008/0015528 A1 | 1/2008 | Chang | | |
| 2011/0152802 A1 | 6/2011 | DiCamillo et al. | | |
| 2012/0029452 A1 * | 2/2012 | Rodsten | ............... | A61F 5/4408 |
| | | | | 604/353 |
| 2013/0237964 A1 | 9/2013 | Kicos | | |
| 2013/0338617 A1 | 12/2013 | Newton, Jr. | | |
| 2014/0163498 A1 | 6/2014 | Natusch | | |

\* cited by examiner

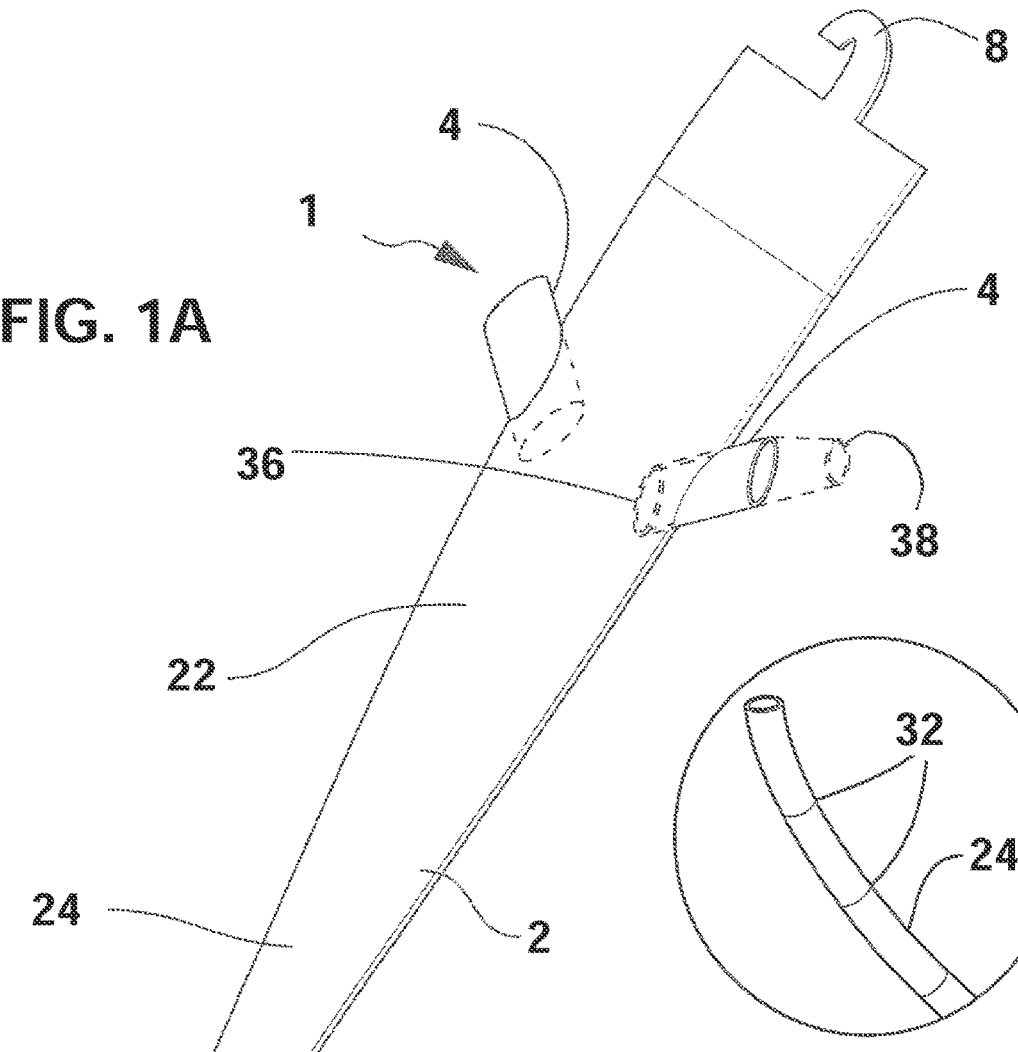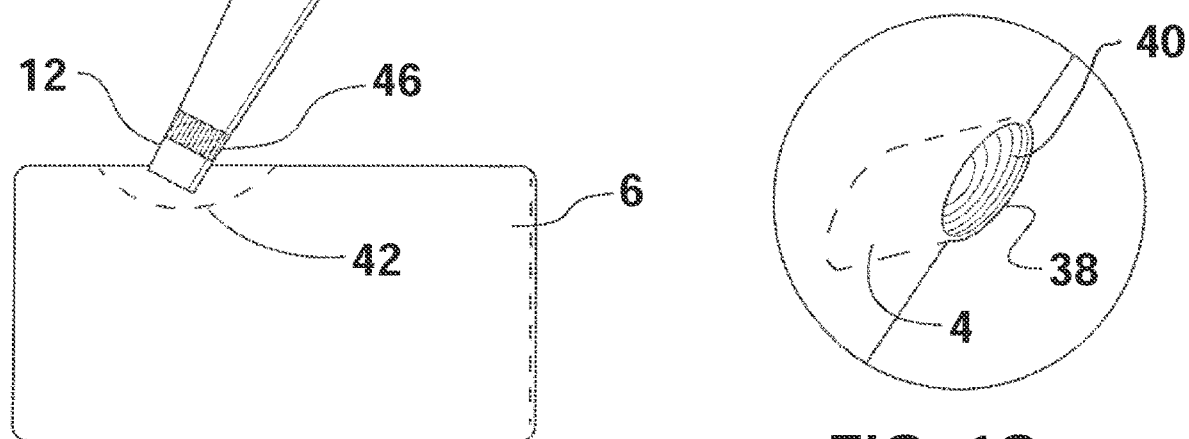

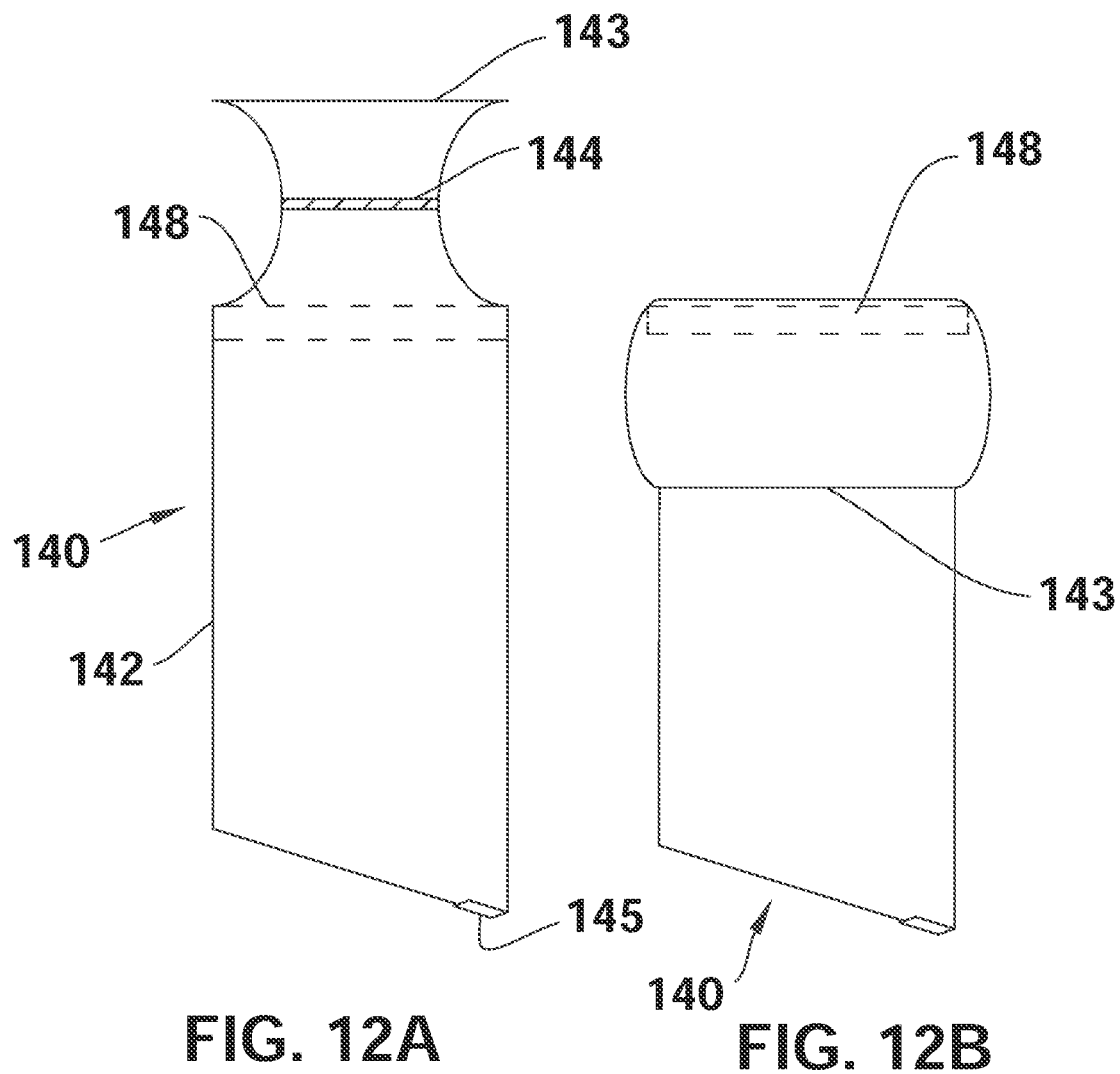
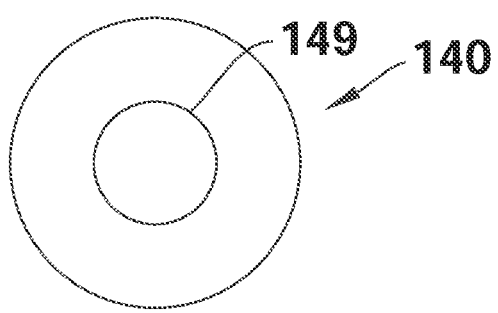
FIG. 12A   FIG. 12B
FIG. 12C

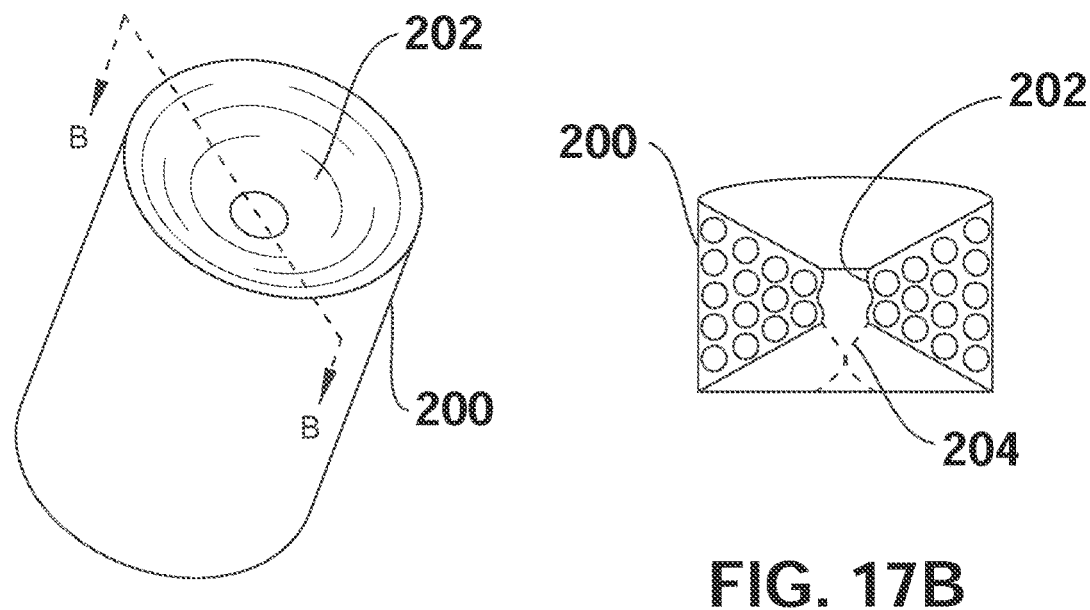
FIG. 17A
FIG. 17B
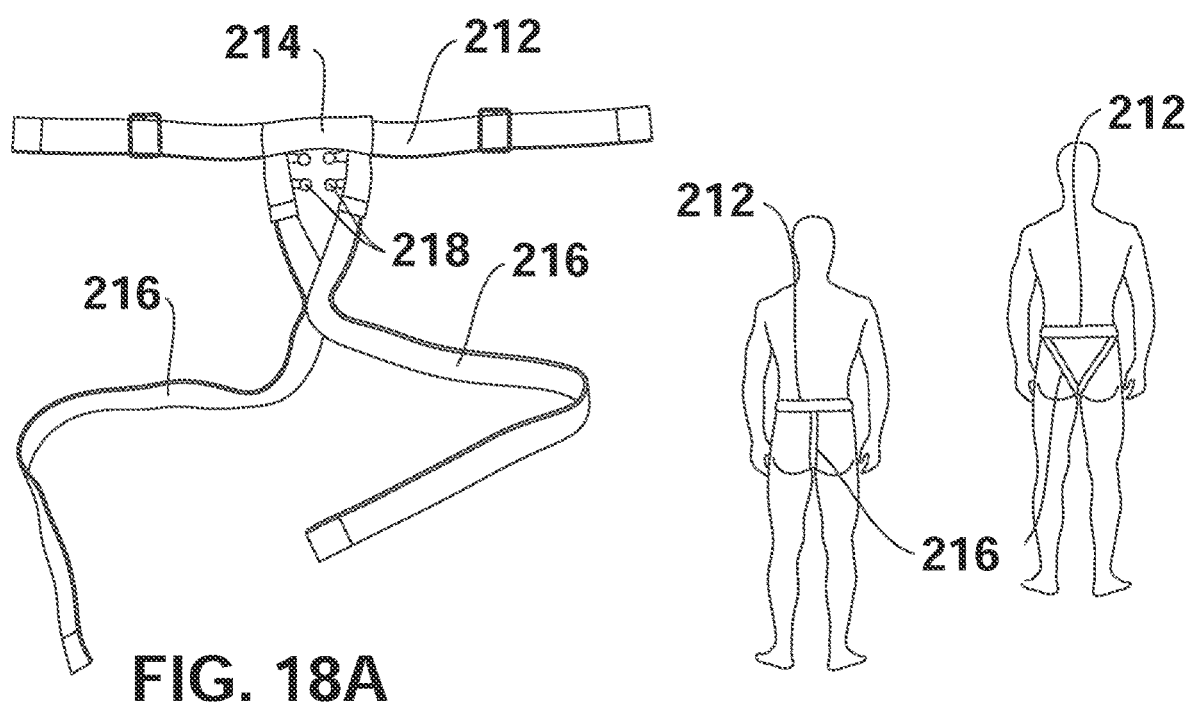
FIG. 18A
FIG. 18B

WEARABLE URINARY COLLECTION APPARATUS

CROSS REFERENCE TO RELATED APPLICATIONS

This application claims priority under 35 USC § 119(e) from U.S. Provisional Patent Application Nos. 63/100,069, filed Feb. 28, 2020 and 63/101,607, filed May 8, 2020. This application is also a continuation-in-part (CIP) application of U.S. patent application Ser. No. 16/376,245, filed Apr. 5, 2019 which claims priority under 35 USC § 119(e) from U.S. Provisional Patent Application Nos. 62/763,239, filed 6 Jun. 2018, 62/763,748, filed 2 Jul. 2018 and 62/765,200, filed 20 Aug. 2018. The entire disclosure of each of the above-mentioned priority applications is incorporated herein by reference.

BACKGROUND OF THE INVENTION

1. Field of the Invention

The present invention relates to an apparatus which may be inconspicuously and conveniently worn by a male or female person beneath regular clothing for receiving and storing urine discharged by the person. More particularly, the present invention relates to a disposable and wearable apparatus of the type described, which can be used by both male and female users who have urinary incontinence or urinary urgency while usual private access for voiding is not available. The disclosed apparatus is simple to use, reasonably comfortable to wear, includes a thin-walled plastic receptacle which may be disposable with an entry port that inhibits backflow and may also include a reusable fabric sleeve that conveniently supports the plastic receptacle adjacent a user's genitals, extends between the user's legs and is conveniently supported on the user's body.

2. Description of the Background Art

A great number of urinary receptacles for men and women suffering incontinence have been on the market for many years and a number of different approaches have been tested, including the basic diaper type products which include liquid-absorbing materials and are worn in contact with a person's genitals. There are various other known devices which are worn by a person beneath the normal clothing some of which include a liquid receptacle that collects urine discharged by the person and which may be subsequently disposed of or emptied for reuse, others of which may be extended over the male organ similar to a condom and which are elongate so that they can channel any discharged urine downwardly to an opening near the person's feet or to a receptacle secured to the person at a lower level, and some devices which may require the assistance of a medical professional such as a catheter. See, for example, the devices disclosed in U.S. Pat. No. 3,356,091, US Published Application Nos. 2008/0015528, 2011/0152802, 2012/0029452, 2013/0237964, 2013/0338617, 2014/0163498, and WO2006077351.

While each of these devices may serve the intended purposes, there are some drawbacks associated therewith. For example, most of the known devices are relatively bulky such that a user feels encumbered when wearing same and at least some part of the device projects away from the user's body, especially in the genital area, so that it becomes conspicuous to others that the person is wearing same, while the conventional apparatus tend to be inconvenient and conspicuous when accessing same for adjustment and the like. Also, some of these devices may remain attached to a person's urinary organ which may become uncomfortable and may lead to other problems such as urinary tract infections. With condom type urinary receptacles that are disposed over the male organ, there may be friction between the male organ and the condom including any adhesive associated therewith, such that inflammation and irritation of the male organ may occur. Further, it may become difficult to attach and detach the device to the male organ if it becomes necessary to use the device multiple times while it is being worn by the person for an extended period. Also, some traditional urinary receptacles such as catheters require the assistance of medical professionals, which makes use of same challenging.

Previously, the applicant has proposed similar devices in U.S. patent application Ser. No. 15/144,889 filed on May 3, 2016 (now U.S. Pat. No. 9,737,433 B2) and U.S. patent application Ser. No. 15/682,010, filed 21 Aug. 2017. While applicant's previously proposed devices provide improvements over conventionally known devices, they still remain to be improved on in terms of convenience in use, comfort, etc. For example, the urinary collection apparatus disclosed in U.S. Pat. No. 9,737,433 B2 include a main body formed of thin plastic sheet material which may be directly supported on a user's body or user's clothing which may be used by itself or together a separate thin walled plastic receptacle that contains urine discharged into the apparatus and/or a supporting pocket that may be attached to a user's leg or the like and supports a separate receptacle therein. While such previously disclosed apparatus function appropriately, they may not give the user a strong confidence that the collection apparatus will surely contain any urine therein when the user is actively moving about, and may otherwise not be fully comfortable or convenient to use.

Thus, a need still exists in the art for a wearable urinary receptacle, which may be inconspicuously and conveniently worn by a male or female person beneath regular clothing for receiving and storing urine discharged by the person, which may be used by essentially any person, which may be conveniently attached and detached to the person's urinary organ multiple times during an extended period of use, which is simple to use, and which may be conveniently and inconspicuously accessed for manipulation while being worn by a user, which gives the user a strong confidence in the ability of the apparatus to surely contain urine while the user is active, is comfortable and does not significantly limit the user's ability to move.

SUMMARY OF THE INVENTION

The present invention has been developed in order to fulfill the discussed need.

An object of the present invention is to provide a collapsible, flexible urinary collection apparatus which may be inconspicuously and conveniently worn by a male or female person beneath regular clothing for receiving and temporarily storing urine discharged by the person, which includes not only a water-tight receptacle for containing urine, but also a fabric support sleeve which encloses the water-tight receptacle in close proximity to the user's genital area for ease of use, is comfortable to wear and inconspicuous to persons other than the user.

Another object of the present invention to provide such an apparatus including a thin-walled plastic receptacle which is disposable and economical to produce, together with a reusable fabric sleeve which conveniently supports the plastic receptacle in close proximity to a user's crotch for ready access, is relatively comfortable to wear, and permits some movement of urine contained therein without leakage or other complication when a user sits, moves, etc.

Still another object of the present invention is to provide a tubular entry port for the thin walled plastic receptacle which may be conveniently secured to and detached from an opening in the fabric sleeve so that a user may easily discharge urine into the plastic receptacle, and which includes means for preventing or greatly inhibiting back flow of urine from in the receptacle back out through the entry port.

According to a first aspect of the present invention, the urinary collection apparatus comprises: an elongate, watertight, flexible receptacle which receives and stores urine therein, and including an entry port near which is configured to receive a user's penis therein in such that urine discharged from the penis flows into the main body via the entry port; a fabric support sleeve which selectively receives the flexible receptacle therein and is configured to extend between the user's thigh's adjacent the user's crotch, including a smaller opening defined in one portion of the support sleeve which is configured to face towards the user's genital area and a larger opening defined in another portion of the fabric support sleeve; a first fastener for securing the receptacle's entry port to the smaller opening defined in one face of the fabric support sleeve so that the user may discharge urine into the flexible receptacle while the flexible receptacle is disposed within the fabric support sleeve; and a second fastener for securing the fabric support sleeve to a user or to a garment worn by the user, wherein the flexible receptacle is watertight and is configured to collapse flat when empty.

According to a second aspect of the invention, in addition to the first aspect, wherein the entry port includes a backflow preventer which extends within the flexible receptacle.

According to a third aspect of the invention, in addition to the first or second aspects, wherein the fabric support sleeve includes a closure provided with the larger opening which may be selectively opened and closed for permitting the flexible receptacle to be inserted into, removed from and manipulated relative to the fabric support sleeve.

According to a fourth aspect of the invention, in addition to any of the first-third aspects, wherein the watertight, flexible receptacle includes a watertight closure which may be selectively opened and closed. For example, if the user desires to empty urine from the receptacle into a toilet, this may easily be accomplished using the closure.

According to a fifth aspect of the invention, in addition to any of the first-fourth aspects, the second fastener includes at least one of a band that may be secured about the user's waist, an elongate strap that may be secured about the user's waist or shoulders, and a fastener which may be selectively secured to a clothing item worn by the user.

According to a sixth aspect of the present invention, in addition to any of the first—fifth aspects, the entry port includes a first end which is fixed to the flexible receptacle and includes an entry opening configured to receive a user's penis therein, and a second end which extends inward of the flexible receptacle and includes a discharge opening which is smaller than the entry opening.

According to a seventh aspect of the present invention, in addition to the sixth aspect, the entry port further includes a support ring disposed coaxially with the entry opening, and the support sleeve includes a fastener which is configured to be selectively secured to the support ring.

According to an eighth aspect of the present invention, in addition to any of the first-seventh aspects, the urinary collection apparatus may further comprise a backflow inhibiting device which is configured to operatively connected to the entry port of the flexible receptacle for inhibiting urine within the flexible receptacle from flowing out of the flexible receptacle through the entry port.

According to a ninth aspect of the present invention, in addition to the eighth aspect, the backflow inhibiting device includes an elongate, flexible, tubular member that is disposed coaxially within the entry port, includes an entrance opening configured to receive a user's penis therein and a discharge opening which is smaller than the entrance opening, and is configured to collapse flat when not in use.

According to a tenth aspect of the present invention, in addition to the ninth aspect, the backflow inhibiting device further includes an elastic constriction at the entrance opening of the elongate, flexible, tubular member in which the user's penis may be inserted for discharging urine into the flexible receptacle through the backflow inhibiting device.

Such urinary collection apparatus according to the first—tenth aspects of the present provides a number of advantages. For example, the elongate, watertight, flexible receptacle may be made of relatively thin, lightweight and inexpensive plastic material because the receptacle is not directly supported on the user, but is indirectly supported on the user via the fabric support sleeve. The elongate, watertight, flexible receptacle may be manufactured inexpensively and discarded after a single use, whereas the fabric support sleeve may be made of stronger, durable materials that and may be accordingly reused. Further, the fabric support sleeve conveniently and comfortably supports the watertight, flexible receptacle in close proximity to a user's crotch for ready access at any time, is relatively comfortable to wear, and permits movement of urine contained therein without leakage or other complication when a user sits, moves, etc. Further, the fabric support sleeve may include the closure in association with the larger opening for inserting, accessing and removing the flexible receptacle, while the fabric support sleeve remains attached to a user. As another example, the apparatus does not protrude to any significant extent from the user and is inconspicuous to persons other than the user, and does not inhibit the user's movements.

The above advantages and other advantages and features of the present disclosure will be readily apparent from the following detailed description of the preferred embodiments.

Intent of Disclosure

Although the following disclosure offered for public dissemination is detailed to ensure adequacy and aid in understanding of the invention, this is not intended to prejudice that purpose of a patent which is to cover each new inventive concept therein no matter how it may later be disguised by variations in form or additions of further improvements. The claims at the end hereof are the chief aid toward this purpose, as it is these that meet the requirement of pointing out the improvements, combinations and methods in which the inventive concepts are found. There have been chosen specific exemplary embodiments of a urinary collection apparatus according to the present invention and specific alternative structures and modifications thereto. The exemplary embodiments chosen for the purposes of illustration and description of the structure and method of the invention are shown in the accompanying drawings forming a part of the specification.

BRIEF DESCRIPTION OF THE DRAWINGS

FIG. 1A is an side perspective view of a urinary receptacle apparatus in accordance with an exemplary embodiment of the present disclosure;

FIG. 1B is a perspective view of a modification to a lower portion of a main body of the exemplary embodiment of FIG. 1;

FIG. 1C is a perspective view of a modification to a tubular port of the exemplary embodiment of FIG. 1;

FIGS. 12A, 12B are front views showing assembly of an optional backflow preventing device for a tubular entry port for a urinary collection apparatus according to another exemplary embodiment of the present invention.

FIG. 12C is a top view of the device in FIG. 12B.

FIGS. 15A, 15B depict another exemplary embodiment of a urine collection receptacle according to the present invention which includes a flowback preventing means in the form of an elongate cap that is provided near the entrance of the receptacle, of which FIG. 15A is a top plan view of receptacle and cap and FIG. 15B shows some details of assembling the receptacle and cap together.

FIGS. 17A, 17B show another type of flowback preventing means according to another exemplary embodiment of the present invention in the form of an elastomeric cap that may be secured around a user's penis, of which FIG. 17A is a perspective view of the elastomeric cap and FIG. 17B is a cross sectional view of the elastomeric cap taken along line B-B in FIG. 17A.

FIG. 18A is a perspective view of a harness according to an exemplary embodiment of the present invention for supporting a urine collection receptacle on a user's body.

FIG. 18B a rear view showing the harness of FIG. 18A secured to the user in different manners.

DETAILED DESCRIPTION OF EXEMPLARY EMBODIMENTS

Figure 2A:
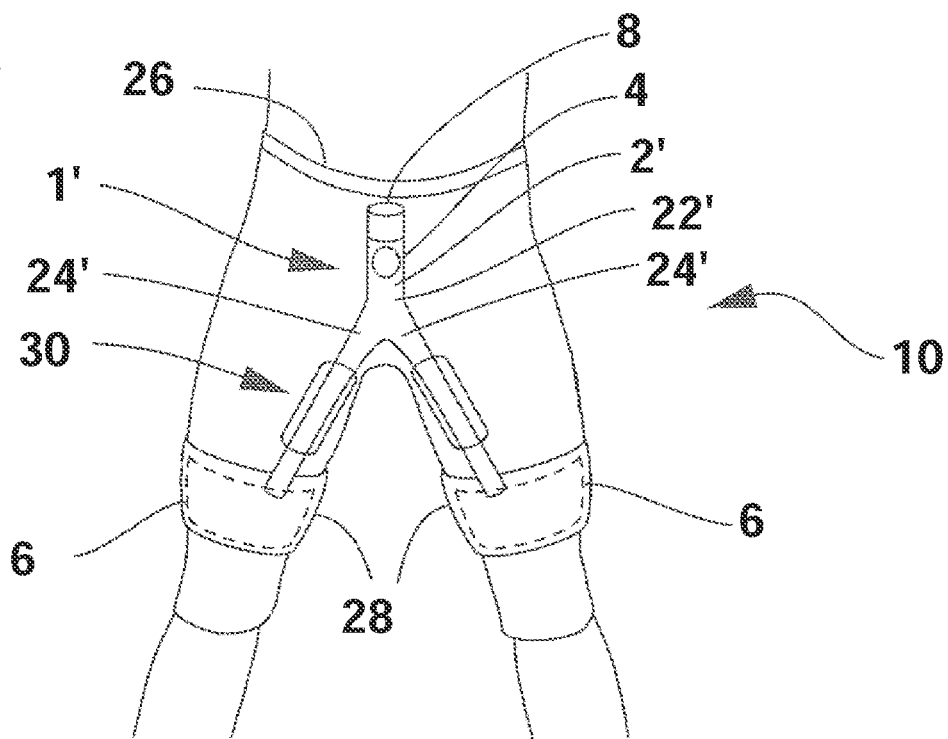
FIG. 2A is a front elevational view of a urinary receptacle apparatus for males according to another exemplary embodiment of urinary receptacle in accordance with the present invention.

As those of ordinary skill in the art will understand, the combinations of features in the illustrated exemplary embodiments of the present invention as disclosed herein are representative of typical applications. However, various combinations and modifications of the features consistent with the teachings of the present disclosure may be desired for particular applications or implementations and are intended to be encompassed within the scope of the present invention, as reflected in the claims appended hereto.

FIG. 1A is an side perspective view of a urinary collection apparatus 1 which may be used by male or female persons in accordance with one exemplary embodiment of the present invention. The urinary collection apparatus 1 may generally include a main body 2, at least one tubular port 4 connected to the main body and projecting therefrom, a urine collection receptacle 6, and securing means for securing the apparatus to a person, such as a fastener 8 which my be used to connect an upper portion of the main body to a an under garment or other garment being worn by the person. The securing means may include other components, e.g., the modified embodiment shown in FIGS. 2A, 2B includes a special under garment 10 which the person would wear and to which the urinary collection apparatus 1 may be connected, as discussed further below.

The urinary collection apparatus 1 may preferably be constructed of flexible and collapsible material(s) which generally remain flat and inconspicuous when the apparatus is worn by a person. Such material(s) may be any suitable material(s), e.g., any suitable type of plastic, plastic-like, rubber, elastomeric, or polymeric material(s), which material(s) may be treated or be treated to possess anti-bacterial properties, including very thin sheet materials such as latex, thermoplastic polyurethane (TPU), high density polyethylene (HDPE), low density polyethylene (LDPE) and linear low density polyethylene (LLDPE) as used in construction of plastic grocery bags, plastic shopping bags and the like. TPU is more stretchable and elastic than HDPE, LDPE and LLDPE, and may be more suitable for use in the present invention as the increases stretchability and elasticity make the collection apparatus more resistant to tearing, and leaking, e.g., so that the receptacle or portions thereof can reliably expand as urine is flowed into it or as the receptacle is moved, sat upon or manipulated. The apparatus 1 may be relatively inexpensive to construct from such material(s), so that it may be disposed of after a single use/wearing, but may be cleaned and reused if desired. Due to the low cost of the materials used to make the urinary collection apparatus 1 in this exemplary embodiment, a user may choose to dispose of the apparatus, or at least some portion(s) thereof such as the storage receptacle 6, after a single use. The urinary collection 1 apparatus may be transparent or any desired color.

The Main Body

The main body 2 may include a larger diameter upper portion 22 to which the tubular port(s) 4 are connected and a lower portion 24 which may taper downwardly to a smaller size and may terminate at a lower open end 12. The lower open end 12 may be in fluid communication with the storage receptacle 6. In terms of shape, the upper portion 22 may be substantially straight such that it may hang directly in front of a user's genitals, and the lower portion 24 may divert left or right toward either of the user's legs, to which the storage receptacle 6 may be secured in any appropriate manner.

The main body 2 may be formed as a tubular sleeve of thin, flexible, waterproof material configured to collapse flat against a user's body when not in use. For example the main body may be formed of pliable sheet material(s) such as discussed above, which may include a single layer or multiple layers laminated together, and which is leak-proof to urine and to other liquids. The upper and/or lower portions of the main body 2 may be constructed from more than one material. Generally, the material(s) used for the main body should be flexible and sufficiently strong and/or stiff so that the main body will retain its general shape, and not become twisted or tangled during any normal physical activities that the user may engage in. Based on its smaller size, the lower portion 24 and especially the lower open end 12 thereof, may be constructed to be stronger and/or stiffer than the larger upper portion 22 to assure that urine may flow unobstructed therethrough, can be repeatedly attached and detached to the storage receptacle 6, and is more resistant to kinking or tangling in its use. While the main body 2 may be sufficiently thin, flexible, and collapsible so that it is unencumbering and inconspicuous in use, again, it should be sufficiently thick and strong that it is not susceptible to leakage and retains its general shape under the forces typically encountered in use thereof.

A diameter of the main body 1 may vary. Generally, the upper portion 22 is sufficiently large so that the tubular port 4 which connects and extends into the upper portion 22 may accommodate a large male organ—penis, or at least a distal portion thereof. For example the upper portion may have a diameter of 8-12 cm and a length of 10-30 cm. The lower portion 24 may then taper to become progressively smaller. For example, the upper end of the lower portion 24 may have the same diameter as that of the the upper portion, then taper downwardly through a length of 10-50 cm or more to a lowermost diameter of 1.0-2.0 cm at the lower open end 12. For an average sized user the lower portion 24 may extend to a mid-thigh, where it would extend into the storage receptacle 6, which receptacle may be secured to the user's thigh or under garment.

When not being used for receiving and channeling urine, the main body 2 collapses flat against the body or under garment of a person wearing the apparatus 1, such that it does not protrude and is inconspicuous. When the main body 2 is being used to collect and channel urine, it will expand slightly as the urine passes through it, but still does not protrude to any appreciable extent and remains inconspicuous.

The upper end of the main body 2 may be closed using any appropriate sealing means such as adhesive or heat to bond the walls of the pliable sheet material together, and a fastener 8 such as a hook, a hook-and-loop fastener, button, etc. may be connected to the upper end of the main body for securing same to a waistline of a garment or under garment worn by the person. With the closed upper end being spaced above the position of the tubular port as shown, any urine in the main body is prevented from leaking from the upper portion of the main body above the port 4. As reflected in FIG. 2A, when the main body 2 is so connected to the garment or under garment worn by the user at substantially a same level as a waistline 26 of the garment, through the fastening means 8 provided on the closed upper end of the main body, the port 4 is conveniently disposed at substantially a same level as the user's penis. The lower portion of the main body may taper downwardly to a smaller size and terminate at the lower open end 12 which may be in fluid communication with the storage receptacle 6.

The lower portion 24, the lower open end 12, and/or the storage receptacle 6 may be provided with a check valve or one-way valve (not shown) to prevent urine from traveling upwardly therein.

Figure 2B:
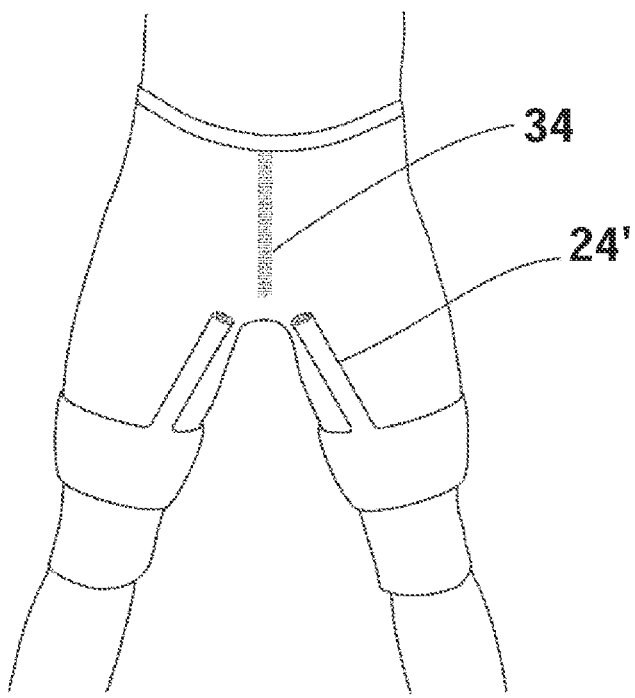
FIG. 2B is a front perspective view of the urinary receptacle apparatus according to the exemplary embodiment of FIG. 2A, but with some components removed for ease of understanding.

While the structure of the exemplary embodiment of the urinary collection apparatus 1 shown in FIG. 1 has been described, it will be apparent to persons of ordinary skill in the art that many modifications and variations may be made thereto with out departing from the intention and gist of the disclosed invention. For example, and with reference to FIGS. 2A, 2B, there is shown a special under garment 10 which the person would wear and to which the urinary collection apparatus 1 or a modified version 1' of the apparatus may be secured such that the tubular port 4 connected to the main body 2' is disposed directly in front of a fly opening 34 of the garment. In FIGS. 2A, 2B a modified version of the urinary collection apparatus is depicted in which the main body 2' includes two of the lower portions 24' which branch off from the upper portion 22' and extend away from each other respectively towards the user's thighs. The under garment 10 may have the general shape of a brief-type under garment which surrounds a user's hips and genitals and extends down to separately surround upper portions of the user's thighs, but could be in the form of boxer shorts, briefs, a jock strap, etc. The garment may include an elastic waistband 26 that secures the under garment around a user's hips, one or more pockets 28 formed of any thin, light material which can receive the storage receptacles 6 therein and are secured to the user's thigh(s) or to portion(s) of the garment surrounding the user's thigh(s), and sleeves 30 made of cloth or thin, light material which respectively cover the lower portions 24' of the main body 2'. The sleeves 30 may be selectively securable around the lower portions 24' of the main body using an appropriate means such as zippers, buttons, or hook-and-loop fasteners, for example. The pockets 28 may have opening(s) through which the collection receptacles may be inserted and removed, and which may also permit the ends of the lower portions 24' of the main body 2' to extend therethrough into the receptacles. In other embodiments, the garment 10 may be an ordinary under garment with elongated pocket(s) 28 provided along the leg part(s) of the under garment, the pocket(s) may be attachable and detachable to the garment 10 by any suitable means, e.g., zipper(s), zip-lock(s), button(s), hook-and-loop fastener(s), etc. The garment 10 may be an ordinary pair of pants provided with side pocket(s) 28, such as discussed below in relation to another embodiment of the invention shown in FIGS. 4-7.

In some embodiments, a strap wraps around the user's waist similar to the elastic waistband 26, thereby holding an upper portion of the urinary collection apparatus 1 against the user. In other embodiments, a strap may be affixed to the user's clothing to hold the apparatus 1 against the user. The strap may be affixed to the receptacle using fasteners, e.g., snaps or buttons, or hook-and-loop fasteners, etc. A single strap may be used, or two or more straps may be used. In some embodiments, the strap may have a fastener to fix the strap to the user's clothing. For example, the strap fastener may be a clip such as used to connect stockings to a garter belt that may be clipped onto underwear to hold the receptacle in place. In a preferred embodiment, the upper end of the main body 2 may be secured to the waistline of the garment by any appropriate means, including a releasable fastener such as a button, a hook, or a hook-and-loop type (e.g., Velcro®) fastener.

Figures 4, 5:
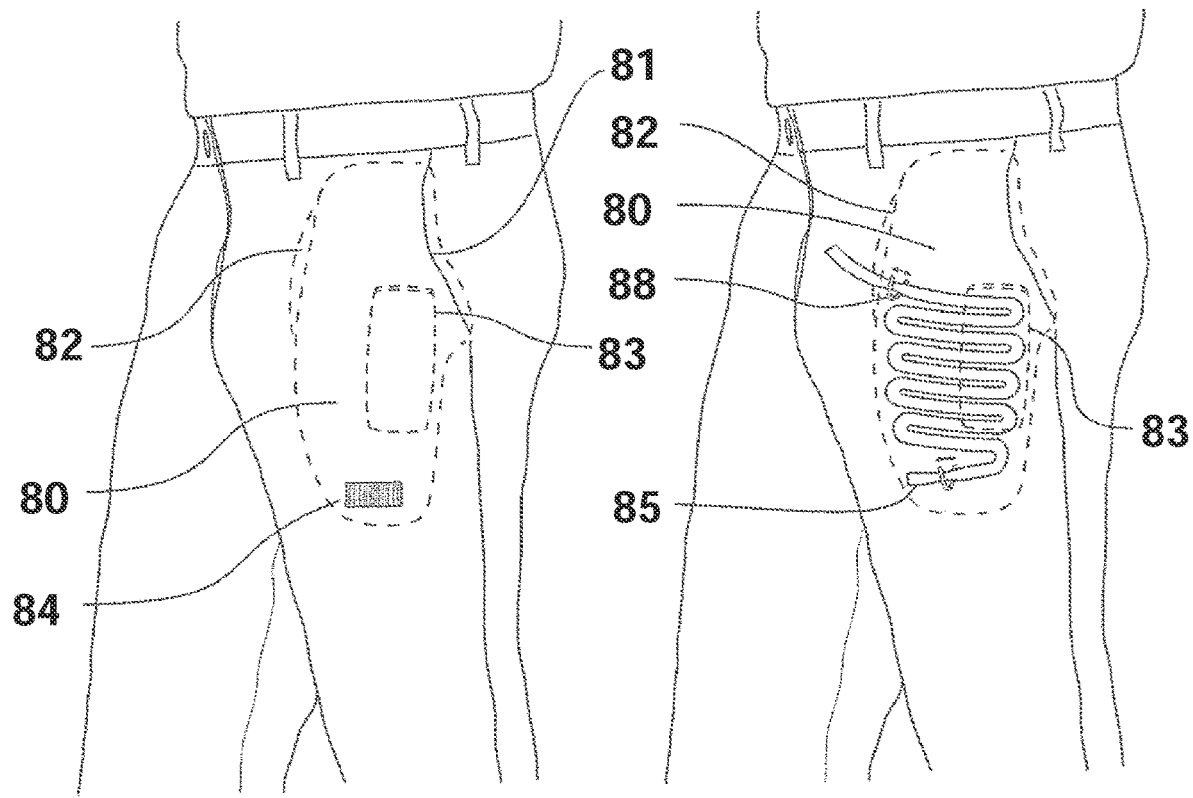
FIG. 4 is a front elevational view of an exemplary embodiment of a garment pocket which may be used as another component of a urinary receptacle apparatus according to the present invention.
FIG. 5 is a front elevational view of the garment pocket of FIG. 4 together with a modification of a portion of the urinary receptacle apparatus of FIG. 1.

The urinary collection apparatus may be worn by a person while he/she is in a non-active mode such as sleeping or a less-active mode such as sitting in a vehicle. In such uses, the collection receptacle 6 may be disposed in spaced relation to the user, e.g., lying on a bedroom floor or vehicle floor, hung on a hanger of known design, or may be disposed outwardly of a garment worn by the user, e.g., hung on the side of a pant leg or pajama leg worn by the user. For such purpose a length of the lower portion of the main body may be at least 50 cm so that it may readily extend to the receptacle which is disposed in spaced relation to the user or outside of the user's outer garment. The exemplarily embodiment of the present invention as shown in FIGS. 4-5 is suitable for such uses because the lower portion of the urine collection apparatus may be easily withdrawn from the outer opening of a pocket of the garment as discussed further herein, and after being withdrawn may be placed on the floor, left to hang from the garment pocket, etc. Of course, the urinary collection apparatus may be used without a collection receptacle, in which case a terminal part of the lower portion of the main body 2 would be disposed in spaced relation to the user or outside of the user's outer garment.

The fastener 8 at the top of the main body 2' of the urinary collection apparatus 1' may be connected to the waistband 26, e.g., if the fastener 8 is a hook-and-loop type fastener one part of the fastener may be connected to the waistband and the other part of the fastener may be connected to the top of the main body.

Another possible modification as shown in FIG. 1 is to include more than one of the tubular ports 4 connected to upper portion 22 of the main body 2, which ports may have different sizes so that an appropriate size port may be used depending on the size of the user's penis, e.g., two different size ports 4 may be disposed opposite to each other on the main body, and the user would wear or secure the apparatus to his body such that the more appropriate sized port is disposed facing the user's penis.

Some possible modifications to the lower portion 24 of the main body 2 include: forming the storage receptacle integrally with the lower portion 24 such that they do not have to be operatively connected and/or disconnected by the user, providing a reinforcement therewith, such as reinforcement rings 32 shown in FIG. 1B, which may be formed of thicker material provided in a spaced manner along the lower portion 24, e.g. every 2-6 cm; the lower portion may be adjustable in length, e.g., by having one or more extensions that can be connected to the lower end 12 via any appropriate fluid-tight means such as a zip-locking fastener; and the lower portion 24 may be closed-ended while the storage receptacle 6 is omitted such that any urine discharged into the main body 2 becomes stored in the lower portion 24 thereof rather than in the storage receptacle, such as in the exemplary embodiment of the invention shown in FIGS. 4-7.

The Tubular Port

The urinary collection apparatus 1 includes at least one tubular port 4 projected from a wall of the upper portion 22 of the main body 2, and is configured to be disposed adjacent to the penis of a male user wearing the apparatus 1 so that the user may easily and conveniently insert at least a distal portion of his penis into the port when desiring to relieve himself into the apparatus. The tubular port 4 may be similar to a condom but it includes two open ends, i.e., one for insertion of the penis and the other which opens into the main body 2 for discharge. Further, the tubular port may include other features which make it suitable for use by persons having different size penises, as well as other features for preventing unintended leakage of urine. A first open end 38 of the port may project outwardly of the upper portion 22 while an intermediate portion of the port 4 is directly connected to the wall of the upper portion 22 and an opposite end 36 may project within the main body as shown in FIG. 1. The first open end 38 of the tubular port may be pushed inside the main body 2 before or after when the tubular port is engaged the user's penis. Of course, many variations are possible, for example, the first open end 38 may be directly connected at and open into a wall the upper portion 22 as the entrance of the port and project inwardly into the main body 2 as shown in FIG. 1C. Inner diameter of the port may be about 4-5 cm with or without stretching, and its length 3-6 cm.

The tubular port 4 may be constructed of various types of material that is flexible, stretchable, thin, resilient, and the like, and thus is comfortable to wear. It may be constructed integrally with the main body 2 using the same material(s) that is/are used to form the main body. Alternatively, and given that the tubular port will normally experience more handling than the main body 2, the tubular port may be made separately from the main body, and of stronger and/or more elastic material(s) than the main body, and subsequently connected to the main body by adhesive bonding, heat bonding, or in any other appropriate manner that will maintain a strong, fluid-tight connection between the components. For example, the tubular port 4 may be made from latex which is the most popular materials for condom so that it can stay secured on the penis like a latex condom. The tubular port 4 may also be made from non-latex material such as synthetic plastic materials such as TPU, rubber, elastomers, etc. If the material(s) used for the tubular port 4 is/are stretchable, this helps to make the tubular port 4 adaptable to receive different size penises, and may help to prevent constriction, discomfort, and displacement of the penis relative to the port 4.

Alternatively and as shown in FIG. 1A, the urinary receptacle 1 may have plurality of tubular ports 4, each of which has a different diameter and/or length to accommodate different sizes of penis. In such a modification involving multiple ports 4, the ports may be provided in spaced manner around a circumference of the upper portion, such that the user could secure the apparatus 1 to his undergarment with the appropriate one of the tubular ports 4 facing toward his penis so that use of the apparatus is facilitated.

As another alternative for making the tubular port usable by persons with different size penises, the end of the tubular port 4 into which a penis is to be inserted may be formed in an elongate, tapering shape which becomes smaller further away from where the port 4 connects to the upper portion 22 such as shown with broken lines in FIG. 1A. The user may then, if necessary, cut off an appropriate terminal part of the projecting end such that the remaining part will have a suitable diameter for receiving the user's penis in a leak-proof manner. Similarly, the end of the tubular port 4 into which a penis is to be inserted may include a plurality of segments with different diameters such as small, medium and large extending continuously from each other such that the smallest segment is the terminal part of the end furthest from the upper portion 22, the medium section is next, and the largest section connects to the wall of the upper portion 22. The small section and medium section may be removed if needed by the user. Still further, the first open end 38 of the tubular port may be pushed inside the main body 2 before or after when the tubular port is engaged the user's penis as discussed above. In any event, the tubular port 4 should have a sufficiently large inner diameter to accept a user's penis comfortably, e.g., it should loosely receive the user's penis and allow space for movement while the user is wearing the receptacle so that it is relatively comfortable, but should not have an overly wide diameter.

The penis insertion end of the tubular port 4 may have a circular entry mouth/lip which may be reinforced with resilient material, such as an elastic band 40, which draws the lip inwardly to some extent as shown in FIG. 1C. The tubular port 4 effectively becomes elastic due to band 40, which seals against the penis and prevents the penis from unintentionally slipping out. The band 40 should not be so constrictive as to cause any undue pressure or discomfort on the penis.

To avoid the pressure on the contact point of the penis, a cushion member or material (not shown) may also be provided to the penis insertion end of the tubular port 4. The cushion member or material may be made of a soft material, e.g., fabric, foam rubber, gel, or other suitably soft material. In some embodiments, the cushion member may be made of a medical grade material, such as an anti-bacterial gel, latex, or silicone type material that may be washed so that the urinary receptacle is hygienic. The cushion member or material may be any suitable thickness, but preferably not so thick as to make the tubular port encumbering to a user or conspicuous when the apparatus 1 is worn by a user. The cushion member or material may be permanently or removably affixed to the penis insertion end of the tubular port 4. Alternatively, a water proof adhesive cushion member or material, such as a band-aid with built in cushion (e.g., 3M® Extra Cushion Flexible Foam Bandages), may be disposed around the penis before inserting to the tubular port 4 to avoid or minimize effect of constricting pressure caused by resilient material.

Because the tubular port 4 is made of the flexible and collapsible material, it gives the user no or minimal raise in the genital area when being used. The structure stated above makes it convenient to separate/remove a penis from the port without dislodging the port 4, even for physically active users. The penis may be pulled out from the main body 2 or tubular port 4 for natural voiding if desired by the user.

Collection Receptacle

Again the lower end 12 of the lower section 24 of the main body 2 may be open and operatively connected to a separate collection receptacle 6, which may be constructed of thin, lightweight materials such as those discussed above as being suitable for constructions of the main body 2, including TPU, HDPE, LDPE, and LLDPE. The receptacle 6 may be bag or a bladder-like structure which is configured to be secured in a pocket 28 or otherwise secured to a user's thigh using an elastic or non-elastic strap that extends around the thigh, for example. The urinary collection apparatus 1 may include one or more collection receptacles 6 such as shown in FIG. 2A. The collection receptacle(s) 6 may be made of flexible and collapsible material like other components of the apparatus, would be of an appropriate size for holding several ounces of urine and may have some type of liquid absorbent material therein such as the absorbents used in disposable diapers. For example, the collection receptacle 6 may have a flat, rectangular shape which has nominal thickness when empty and a size of 15×15×1.5 cm in dimension or larger when filled with urine. In some embodiments, for small incontinent leaking urine volume, the collection receptacle 6 may have a smaller size. Also, the receptacle 6 may be may be constructed integrally with the lower portion 24 of the main body 2 so that it is not necessary to connect or disconnect same, and the lower portion 24 of the main body 2 may be closed-ended such that urine is stored directly in the lower portion of the main body.

For connecting the lower open end 12 of the lower portion 24 of the main body 2 to the collection receptacle 6, the receptacle 6 may have an opening 42 provided therein which is sized to receive the lower open end 12 therein in a fluid-tight manner, but which permits the receptacle to be easily separated from the lower open end 12 for being emptied or replaced as needed. For this purpose some type of seal 46 may be provided with the lower open end 12 and/or with the opening 42, which seal would require little or no manipulation by a user. Still further, the opening 42 of the receptacle 6 may include a seal which permits the opening 42 to be fluid-tightly closed when desired, e.g., when the receptacle 6 contains urine and is to be removed for replacement or emptying. For example, a zipper-lock type seal or a urine-resistant adhesive could be used.

The receptacle 6 may be selectively attachable to and detachable from the lower portion 24, e.g., to the lower open end 12 of the lower portion 24. The receptacle 6 may attach/detach to the lower portion 24 by a lure lock, snap lock, or other device known in the art which allows quick connection/disconnection of lower portion 24 from the storage receptacle 6 while providing a fluid-tight seal while connected.

The collection receptacle 6 and/or the lower portion 24 of the main body 2 may be equipped with a backflow preventing device, such as the device 140 disclosed in relation to FIGS. 12A-12C, and 15A-17B. The backflow preventing device may be of any suitable design as long as it substantially prevents the flow of urine from the collection receptacle 6 back up toward the lower open end 12 of the lower portion 24 of the main body 2. Generally, backflow is minimized by disposing the collection receptacle 6 at a level significantly below the user's penis. Any suitable type of backflow preventing device may be used, and furthermore, one or more of such backflow preventing devices may be present at any suitable position(s) in the system.

Female Adapter

Figure 3A:
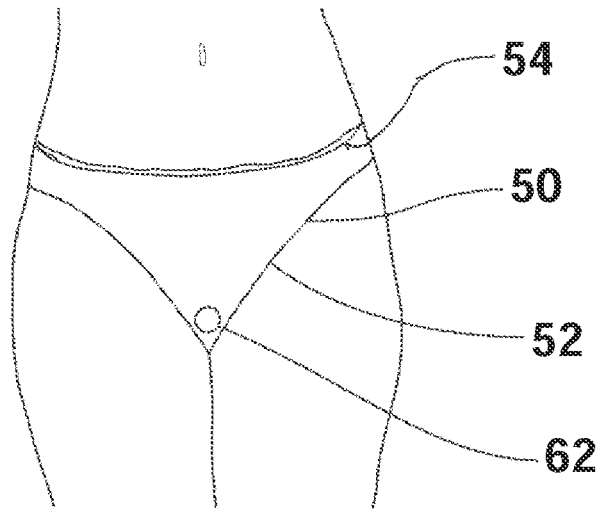
FIG. 3A is a perspective view of one portion of a female adapter which may be used with the urinary receptacle apparatus of FIG. 1.
Figure 3B:
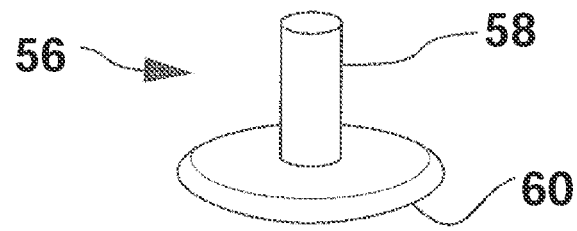
FIG. 3B is a perspective view of another portion of the female adapter which may be used with the urinary receptacle apparatus of FIG. 1.
Figure 3C:
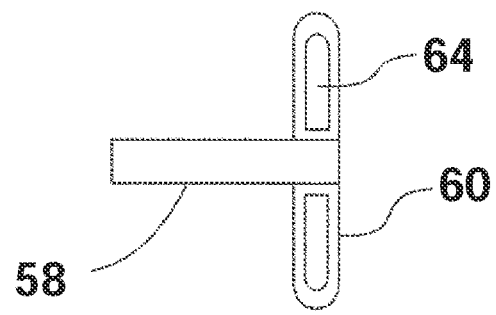
FIG. 3C is a cross section view of the other portion of the female adapter shown in FIG. 3B.
Figure 3D:
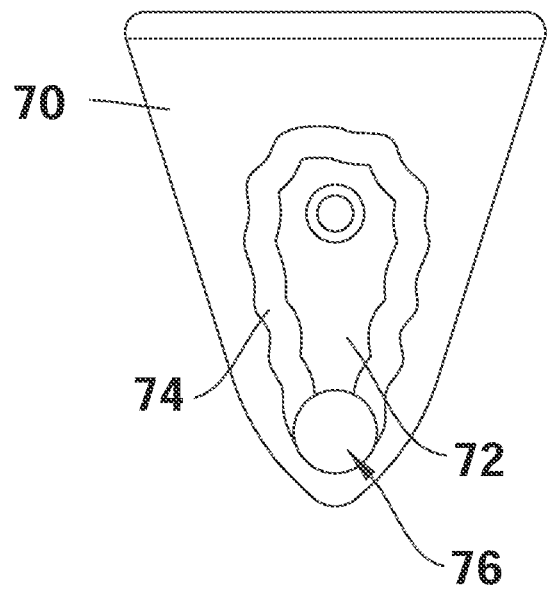
FIG. 3D is a front view of a urethral pad which may be used as an alternative component of the female adapter shown in FIGS. 3A-3C.
Figure 3E:
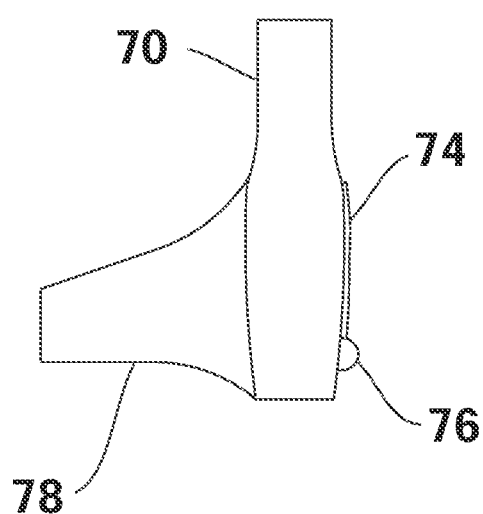
FIG. 3E is a side view of the urethral pad shown in FIG. 3D.

While the urinary collection apparatus 1 as discussed above is particularly suited for use by male persons, the present invention also includes an adapter which may be worn by female persons so that they also can use the urinary collection apparatus 1. One exemplary embodiment of the adapter is shown in FIGS. 3A-3C, while a second exemplary embodiment is shown in FIGS. 3D-3E. Referring to FIGS. 3A-3C, the first exemplary female adapter may include a first part 50 and a second part 56 which may be used in combination. The first part 50 may be worn by a female similar to a panty, includes a main body 52 which is shaped to be provided in covering relation to the female genital area, an opening 62 formed through a central portion thereof, and an elastic waistband 54 connected to the main body and which the female user would wear about her hips or waist. The second part 56 includes a base pad 60 and a spout 58 which projects from the base 60 and extends through the opening 62 when the second part 56 is joined with the main body 52 so that the spout 58 would project from the opening 62. With such structure the female user could easily manipulate the spout into the tubular port 4 of the urinary collection apparatus 1 similar to the male penis when the female user desires to discharge urine into the apparatus 1.

The base pad 60 may be disposed between the first part and the third part so that it contacts against the rear side of the third part and the spout 58 may be connected to a center of the base pad in a fluid—tight manner, such that it projects away therefrom and extends through the opening 62. The base pad 60 may be made of any material which would not cause discomfort to the female user when worn for several hours at a time, e.g., cotton or a soft, spongy polymer material, and may be used together with a soft pliable substance such as a gel for comfortable, secure and easy positioning of the base pad over a female's urethral region. As depicted in FIG. 3C the base pad 60, may contain therein an air-filled bladder 64 or other elastic cushion material to minimize any discomfort to the user. The base pad 60 provides a sufficiently tight contact with the urethral region that any urine discharged by the user would be guided to flow through the spout 58. The base pad 60 may be flat and significantly wider than the spout 58 as depicted.

Referring to FIGS. 3D-3E, a female adapter in this exemplary embodiment includes a substantially triangular shaped urethral pad 70 which may be used together with the first part 50 of the other exemplary embodiment. The pad 70 is large enough to cover and fit to the general area of a female's urogenital region and would be disposed within the main body 52 of the first part 50 such that a front side thereof, as shown in FIG. 3D, engages a female's urogenital region while the rear side thereof, including spout 78, faces away from the user so that the spout 78 provided on the rear side may extend through the opening 62 of the first part similarly to the spout 58 of the other embodiment. The urethral pad 70 may be made of any material which would not cause discomfort to the female user when worn for several hours at a time, e.g., cotton or a soft, spongy polymer material, and may be used together with a soft pliable substance such as a biocompatible adhesives like hydrogel gel for comfortable, secure and easy positioning over a female's urethral region.

Referring to FIG. 3D, in a lower center of the front face of the pad 70, where it would align with the female user's urethral vestibule, an opening 72 may be provided which may be generally triangular or oval in shape. As depicted, the opening 72 may be disposed closer to a lowest point of the triangular shaped pad and roughly aligned between two legs of the triangular pad which converge toward a low point of the pad. The opening may have a size such as 2.5-5 cm inches long and 2.5 cm wide. A circumferential border of the opening 72 may include means for helping to direct urine toward the opening and for preventing urine from flowing away from the opening. For example, a continuous string of small elastic projections 74 closely tied each other may be provided which surround the opening 72, each of the projections 74 may be 1-2 mm wide and high, and at least one larger size elastic projection 76, e.g., 4-6 mm wide and high, located closest to the low point of the pad 70. The larger ball(s) 76 are may be placed in the female user's vestibular area between labia for properly locating the opening 72 relative to the user.

Referring to FIG. 3E, the rear side of the pad 70 includes the spout 78, which may be formed of plastic and generally funnel-shaped such that it encompasses and overlays the rear side of the opening 72. The spout 78 may be firmly affixed to the front side of the pad 70 in any appropriate manner, e.g., a base of the spout 78 may be provided with a circumferential outer rim and may be adhesively bonded to the rear side of the pad in surrounding relation to the opening 72. Also, the spout may be reusable and means may be provided to attach the spout to the pad such as a reversible clamp which connects the spout's circumferential outer rim the rim together with an outer fringe of the pad 70.

Embodiments Without Separate Collection Receptacle

With reference to FIGS. 4-7, there is shown another exemplary embodiment of the urinary collection apparatus according to the present invention which does not include a separate collection receptacle, but instead the lower end of the lower portion 24 of the main body 2 may be closed or closable so that urine discharged into the main body through the tubular port 4 may be securely collected and retained in the lower portion 24. In other words, the main body of the collection apparatus is a urine collecting and storing receptacle itself. Additionally, means are provided whereby a user may simply and inconspicuously access the apparatus for any necessary or desired manipulation of same. Particularly, as depicted a side pocket 80 provided with a conventional outer garment for covering a user's lower body, such as pants, shorts, or a skirt, may be provided with an inner access opening 82 in an upper portion of the pocket and which opens to the inside of the outer garment, as well as a conventional outer access opening 81 of the pocket which opens to the outside of the garment such that a person wearing the garment may insert his/her hand into the pocket 80 through the opening 81. In this embodiment the closed-ended lower portion 24 of the main body 2 may be inserted into the pocket 80 through the inner access opening 82 where it may remain until the user removes the urinary collection apparatus.

Further, a securing means may be provided with the pocket 80 and/or the lower portion 24 of the main body for securing the closed lower end of the lower portion 24 within the pocket.

Figure 7:
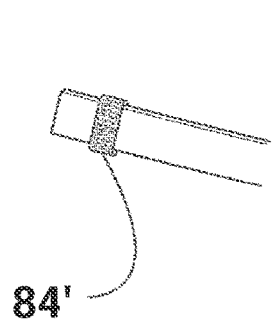
FIG. 7 is similar to FIG. 6 and shows a modification of the embodiment in FIG. 6.
Figure 6:
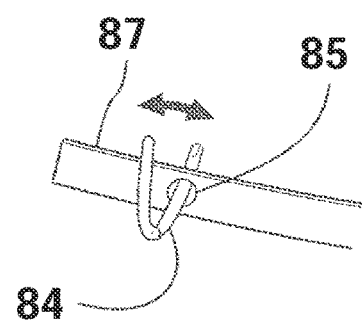
FIG. 6 is an enlarged front elevational view showing how the components in the modified exemplary embodiment of FIG. 5 may be coupled together.

Such securing means may, for example, include an opening or slit 85 provided through an extension 87 of the lower closed end of the lower portion 24, which extension 87 is not in fluid communication with the rest of the lower portion 24, and a manipulatable coupler 84 secured within the pocket 80 and which may be easily manipulated by a user with one hand inserted into the pocket for operatively connecting the coupler 84 through and about the opening 85, and for opening the coupler to disconnect it from the opening 85 as shown in FIG. 6. Alternatively the opening or slit 85 may instead be provided in a member (not shown) connected to the inside of the pocket 80, while the manipulatable coupler 84 is connected to the lower end 24 of the main body. Further, other securing means could be provided for securing the closed lower end of the lower portion 24 within the pocket. Some other examples include a button (not shown) secured within the pocket 80 and which may be inserted through or withdrawn from the opening or slit 85 for selectively connecting and disconnecting the lower end of the lower portion 24 within the pocket, a hook-and-loop type fastener 84' as shown in FIG. 7 with respective portions connected to the closed lower end of the lower portion 24 and the pocket, etc. Also, the pocket 80 may have a second smaller pocket 83 attached to an inner surface thereof for storing small personal items or the like, and an additional securing means may be provided such that another part of the closed lower end of the lower portion 24 may be secured to the smaller pocket.

As shown in FIG. 5 the lower portion 24 of the main body 2 as retained inside of the pocket 80 may have an extended length which is accommodated by arranging the closed lower end in serpentine fashion within the pocket 80. An extended length is not necessary, however, and the lower portion 24 of the main body 2 may simply extend within the pocket 80 without any twists or turns, it may be constructed with a larger diameter to hold more liquid, etc. The closed-end lower portion 24 of the main body 2 may expand somewhat when filled with urine, but not so much that it would protrude and become conspicuous. Additionally, the pocket 80 may include some type of closure means 88 for being selectively connected to the lower portion 24 for closing off a section of the lower portion 24 which contains urine therein, as an added precaution for preventing the urine from moving back upwardly in the lower portion 24. Such closure means may also function as the securing means, or one part thereof, which secures the lower portion 24 in the pocket 80 and may, for example, comprise a manipulatable member similar to member 84, or any other appropriate closure means. For example, the closure means may comprise a spring lock mechanism (not shown), such as the spring lock mechanisms commonly used with apparel, e.g., as adjustable waistbands, adjustable hood bands, etc., having a cord which may be disposed around a part of the lower portion, a receiver having an opening defined therethrough and through which ends of the cord may be inserted, and a spring-biased member disposed within the receiver and which is normally urged into locking engagement with portions of the cord extended through the opening. For closing off the urine-containing part of the lower portion 24, the spring-biased member is compressed, e.g., between the user's thumb and index finger, the cord is extended around an appropriate part of the lower portion, the cord ends are inserted and pulled through the opening in the receiver so that an intermediate portion of the cord is drawn to a tight constriction about the part of the lower portion, and then the cord is locked in place by releasing compression on the spring-biased member so that it moves into locking engagement with the cord ends. Some portion of the closure means may also be connected to the pocket.

While in the embodiment of FIGS. 4-7 the apparatus does not include a separate receptacle and the lower end 12 of the lower portion 24 of the main body is closed such that urine is collected and retained in the lower portion, it is apparent and within the scope of the present invention that the embodiment of the invention as shown in FIG. 1 including the separate receptacle 6 could also be used together with the outer garment having the side pockets 80 as shown in FIGS. 4-5. For example, the receptacle 6 and the lower portion 24 of the main body 2 could be disposed and secured in the side pocket 80 during use of the apparatus 1.

As mentioned above the lower portion 24 of the main body may be closable rather than permanently closed. For example, the lower open end 12 of the lower portion may be provided with a zipper locking-type, fluid-tight sealing means such as the closure 106 shown in FIG. 9, which a user may easily close or open as desired, e.g., the sealing means would be closed when the user desires urine to be collected and retained in the lower portion 24, and may be opened when the user desires to empty the collected urine from the lower portion. Thus, for example, urine may be collected and retained in the lower portion 24 (as situated within or outside of the pocket) when the user is unable to access a restroom or the like, but if the user later is able to access a restroom, he/she may conveniently remove the lower portion 24 from the pocket 80 by disconnecting the securing means which retains the lower portion in the pocket, and extending the lower portion 24 through the outer opening 81 of the pocket, after which the lower end 12 of the lower portion 24 may be disposed over a toilet and the sealing means opened to allow the collected urine to be discharged into the toilet. The sealing means again be closed and the lower portion re-secured within the pocket 80 for further use.

Figure 8:
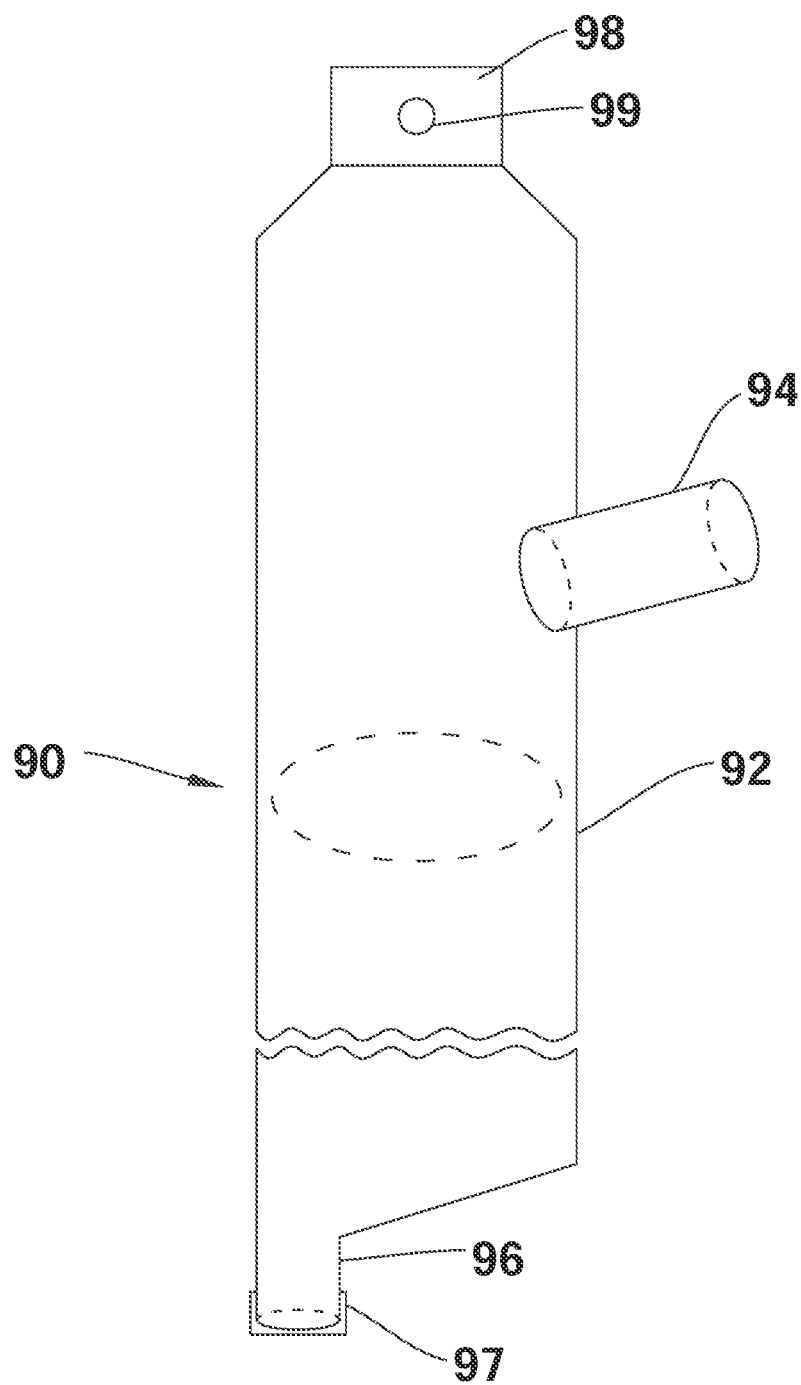
FIG. 8 shows a urinary collection apparatus according to another exemplary embodiment of the present invention.
Figure 9:
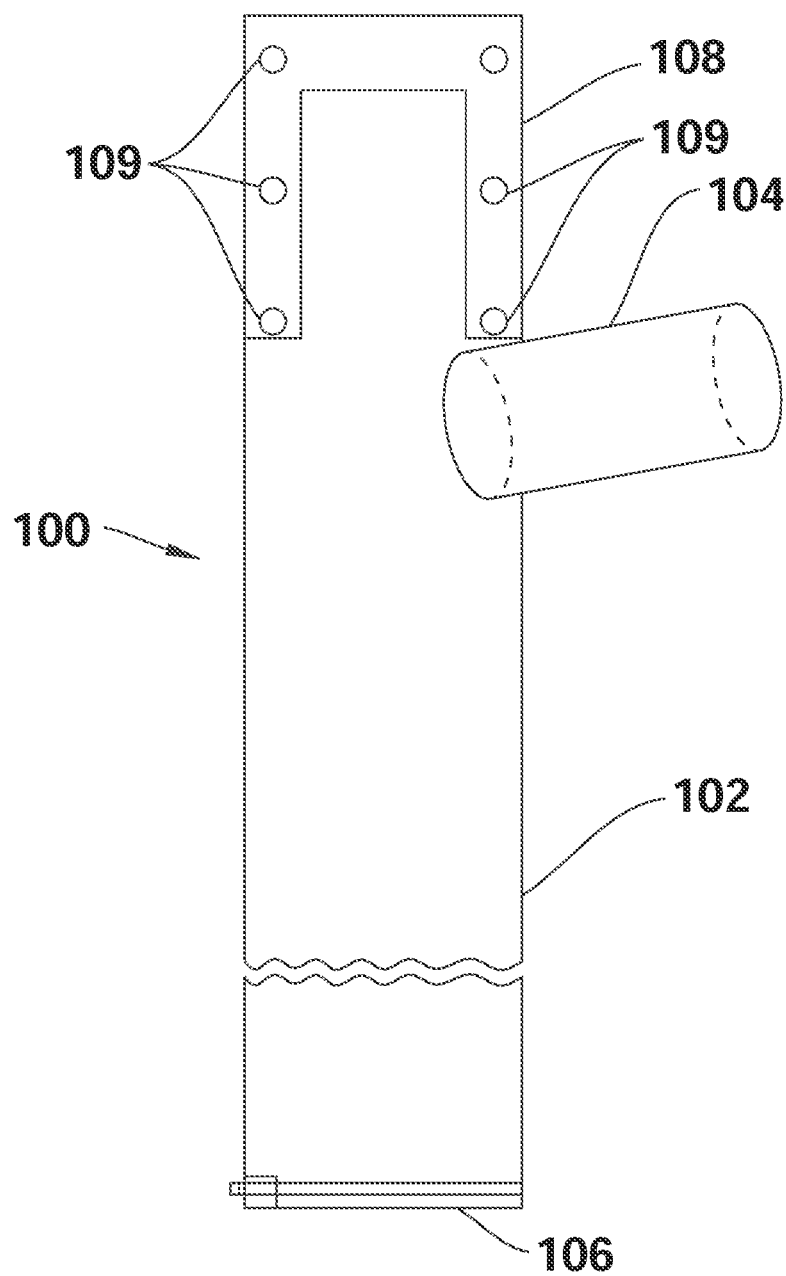
FIG. 9 shows a urinary collection apparatus according to another exemplary embodiment of the present invention.

With reference to FIGS. 8 and 9, there are shown two other exemplary embodiments of the urinary collection apparatus according to the present invention which function as the urine-containing receptacle itself and hence do not include a separate urine collection receptacle. These embodiments also include a tubular entry port positioned at an intermediate portion thereof. These embodiments have a more simple structure and may be more easily constructed than the other embodiments discussed above.

A collection apparatus 90 as shown in FIG. 8 includes a main body 92 having a tubular entry port 94, a lower end that tapers to a discharge port 96 and a tapered, reinforced upper portion 98 provided integrally therewith. The main body 92 may be easily constructed of thin, lightweight plastic materials such as latex, TPU, HDPE, LDPE, and LLDPE, e.g., provide two sheets formed of the plastic materials and each including ½ of the tubular entry port 94, ½ of the discharge port 96 and ½ of the reinforced upper portion 98 and then bond the two sheets together at their peripheries by any appropriate means including heat, adhesives, etc. The tubular port 94 may have a substantially cylindrical shape with one end fixed to the main body as depicted. Such tubular port 94 may be easily inverted to extend within the main body 92, such as the tubular port 4 in FIG. 1C, where it would also function to help prevent backflow of urine from in the main body 92 back out through the entry port. Additionally, the tubular entry port 94 may taper from a larger diameter where it is connected to the main body to a smaller diameter at its free end such as with the tubular port 4 shown at 38 in FIG. 1B. The main body 92 may be sized to hold any suitable amount of urine such as 200-400 ml, and may have an elongate shape such as 5-9 cm in diameter and 20-40 cm in length. Additionally, the collection apparatus 90 may be provided in different sizes, so that a suitably sized apparatus 90 may be used depending on how much urine it may be required to hold. The upper portion 98 may be reinforced by addition of any suitable reinforcing material such as fibers and/or a thicker plastic sheet, and one or more openings 99 may be defined through the upper portion 98 to securely receive some type of fastener (not shown) that would also be secured to a user or a user's garment, e.g., a strap that may be secured about the user's waist, a clip that secures to a waistband of a user's underwear garment, etc. A closure 97 may be selectively secured to the discharge port 96 in a fluid-tight manner or removed from the discharge port 96 to permit urine stored in the main body 92 to be emptied out. The closure may have any suitable structure, e.g., a clip (not shown) which securely clamps the discharge port 96 shut, and the discharge port 96 may be sufficiently long so that it may be folded onto itself one or more times before the clip is applied.

A collection apparatus 100 as shown in FIG. 9 includes a main body 102 having a tubular entry port 104, a lower end having a closable discharge port 106 and a reinforced upper portion 108 provided integrally therewith. The collection apparatus 100 is very similar to the collection apparatus 90 in FIG. 8, except that its upper portion and its lower portion including the closable discharge port 106 do not taper to smaller diameters in comparison to other portions thereof, a sliding-type closure is provided integrally with the closable discharge port 106 rather than being a separate component which must be connected to the discharge port, and the reinforced upper portion includes multiple openings 109 defined therethrough that are spaced apart from each other so that different ones of the openings may selectively receive a suitable fastener (not shown) that would also be secured to a user or a user's garment, e.g., a strap that may be secured about the user's waist, a clip that secures to a waistband of a user's underwear garment, etc., for appropriately positioning the apparatus 100 relative to a user's penis. Again, the collection apparatus 100 may be manufactured relatively easily from thin, lightweight plastic materials such as latex, TPU, HDPE, LDPE, and LLDPE such as described in relation to the collection apparatus 90 in FIG. 8. The sliding-type closure at the discharge port 106 is particularly convenient because a user would only be required to slide the closure to an appropriate position for opening and closing the discharge port 106, without having to attach the closure to the discharge port.

Figure 10B:
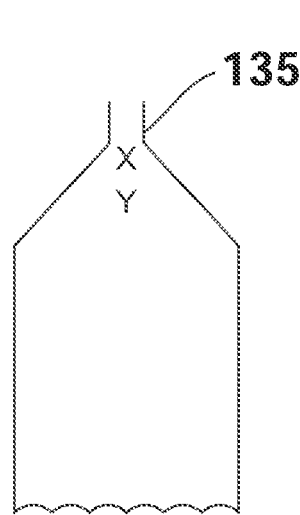
FIGS. 10A-10C are front views depicting assembly steps of another exemplary embodiment of a urinary collection apparatus according to the present invention including a tubular entry port disposed at one end thereof.
Figure 10C:
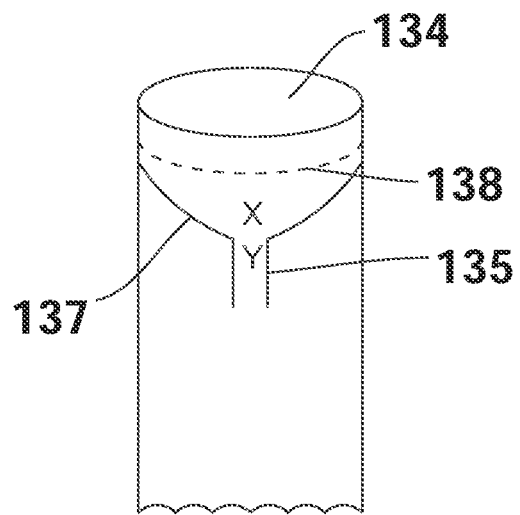
Figure 10A:
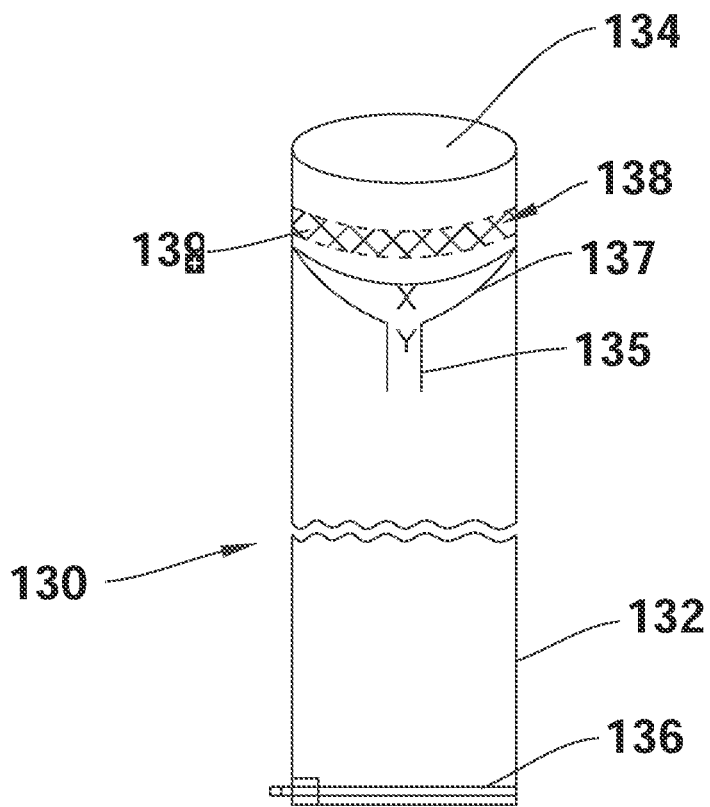

With reference to FIGS. 10A-10C, there is shown another exemplary embodiment of a urinary collection apparatus 130 according to the present invention which functions as the urine-containing receptacle itself and hence does not include a separate receptacle. Primary differences between this apparatus 130 and the urinary collection apparatus 90, 100 of the embodiments disclosed in relation to FIGS. 8, 9 include that the apparatus 130 has a tubular entry port 134 positioned at one end thereof, rather than at an intermediate portion thereof, and has a more simple structure that may be more easily constructed and manipulated than the apparatus of the other embodiments.

The urinary collection apparatus 130 as shown in FIGS. 10A-10C includes a main body 132 integrally including a tubular entry port 134 at one end of the main body having an extension 137 which extends within the main body, and an opposite end of the main body having a closable discharge port 136. Additionally, a support ring 138 may be provided in association with the tubular entry port 134, and the ring 138 may include an annular groove 139 on an outer surface thereof which could be used for securing the tubular entry port 134 to a support sleeve such as discussed below in relation to FIGS. 11A-11B. Again, the main body 132 of the collection apparatus 130 may be manufactured relatively easily from thin, lightweight plastic materials such as latex, TPU, HDPE, LDPE, and LLDPE such as described in relation to the apparatus 90 in FIG. 8. The ring 138 may be formed of a rigid or semi-rigid material such as a plastic, rubber or elastomer.

A lower portion of the main body including the discharge opening with the closable discharge port 136 as shown in FIG. 10A may be essentially the same as the lower portion of the apparatus 100 including the closable discharge port 106 as in FIG. 9. An upper portion of the main body including the tubular entry port 134 may be constructed as shown in FIGS. 10B-10C. Initially, the main body 132 may be formed such that the upper end tapers to a narrow central opening 135 at its uppermost point as shown in FIG. 10 B. Then the support ring 138 may be disposed within the main body, e.g., by being inserted through the closable discharge port 136, and moved to an appropriate position some distance from the central opening 135, e.g., 10-20 cm away, and then the portion of the main body above the ring 138 is folded—inserted though the inner opening of the ring into the main body such that the upper portion of the main body including the central opening 135 now extends down into the main body as part 137 of the tubular entry port 134 as shown in FIG. 10C. With such construction, the tubular entry port 134 can also effectively function as a backflow preventing or inhibiting means as it will be very difficult for urine within the main body to flow into the narrow central opening 135 and back out through the tubular entry port 134. The longer the tubular entry port, including the central opening, extends down into the main body, the more difficult it will be for urine to enter and back flow through the entry port. An adhesive may be applied between the support ring 138 and the tubular port 134 for maintaining the support ring in relative position to the entry port.

Support Sleeve

Figure 11A:
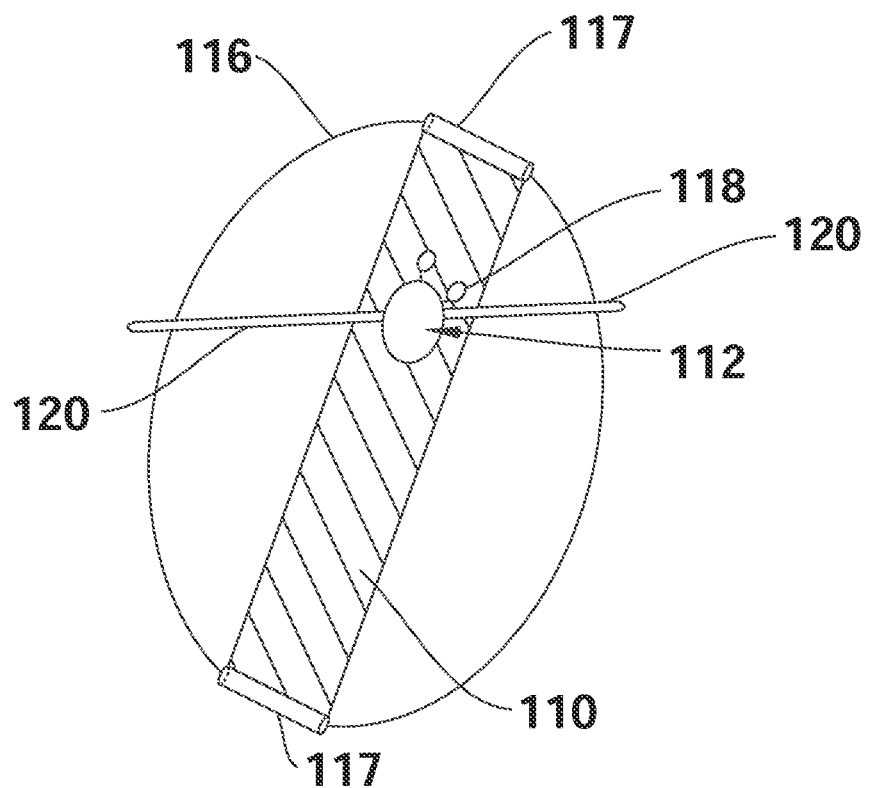
FIG. 11A is a top perspective view of a support sleeve which may be used as another component of a urinary receptacle apparatus according to the present invention, together with an attaching band for the support sleeve.
Figure 11B:
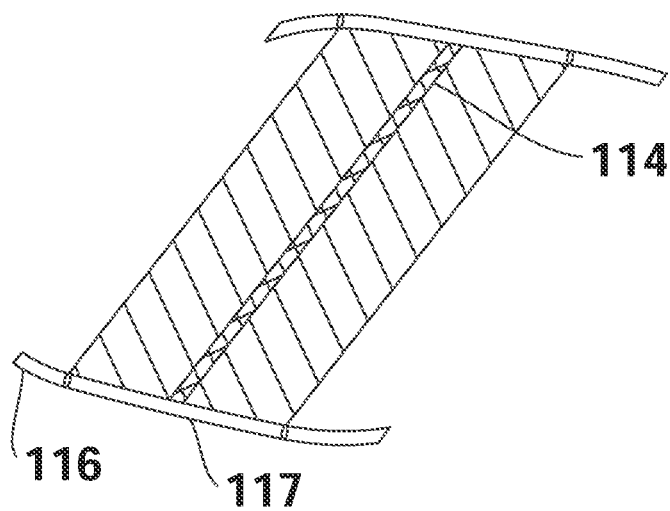
FIG. 11B is a bottom perspective view of the support sleeve of FIG. 11A.

Referring to FIGS. 11A, 11B there is shown an exemplary embodiment of a fabric support sleeve 110 according to the present invention which may be use for conveniently supporting and securing a urine collection apparatus or receptacle such as shown in FIGS. 8, 9 and 10A-10C to a user, male or female, together with a waistband 116 which is connected to the fabric support sleeve and may be selectively secured about a user's waist for supporting the support sleeve on the user's body. While the exemplary embodiments of the urinary collection apparatus according to the present invention as shown in FIGS. 1A-5, 8 and 9 may be directly supported on a user or a user's garment and will function appropriately, they may not give the user a strong confidence that the collection apparatus will surely contain any urine therein when the user is actively moving about, and may otherwise not be fully comfortable or convenient to use. The fabric support sleeve 110, when used as part of the urinary collection apparatus for supporting the water-tight urine receptacle therein, gives the user a strong confidence in the ability of the apparatus to surely contain urine while the user is active, is comfortable and does not significantly limit the user's ability to move.

The fabric support sleeve 110 is designed and intended to enclose an entire urine collection receptacle therein, unlike the small sleeves 30 in FIG. 2A which only surround small portions of a collection receptacle, and the fabric support sleeve comfortably secures the urine collection apparatus in close proximity to the user's genital area, e.g., it is configured to extend between a user's thighs in surrounding relation to the user's genital area from pubis to sacral region, such that the user may easily discharge urine into the collection receptacle whenever the there is an urge or need to do so, while minimizing any concern that the collection receptacle may not be sufficiently secured to the user and/or that collected urine may flow back out of the collection apparatus. To facilitate such use, on a front side of the support sleeve 110 which faces and engages the user's genital area there may be provided a small opening 112 which may receive and have secured thereto the tubular entry port of a urine collection apparatus such as shown in FIGS. 8-10C such that the user may, for example, simply insert his penis into the tubular port and relieve himself. On a rear side of the support sleeve there may be provided a large opening 114 which may be used for inserting a urine collection apparatus into the support sleeve and for accessing, manipulating and removing the urine collection apparatus from the sleeve. Apart from the openings 112, 114 the sleeve may be closed.

The fabric support sleeve 110 sleeve may have a substantially flat and elongate shape, e.g., a flat width of about 7-10 cm and a depth of 2-3 cm such that its inside diameter may expand to about 5-6 cm, and a length of about 30-60 cm. The fabric support sleeve may be made of soft, flexible fabric which will not cause any discomfort to a user when it engages against the user's inner thighs and genital area during use. For example, soft, plush fabric made of cotton, polyester or other material. The inner surfaces of the support sleeve may be coated and/or lined with an appropriate waterproof material such that the support sleeve is watertight except for the opening 112 on its front side, although it is not required that the fabric support sleeve include any waterproof characteristics as the urine receptacle according to the present invention is appropriate for reliably retaining urine therein.

Referring to FIG. 11A, the opening 112 provided on the front side of the fabric support sleeve may be located at an intermediate portion of the sleeve and may have a diameter which is slightly larger than the diameter of the tubular entry port of a collection apparatus so that the entry port can be flush or protrude slightly from the opening such that the entry port may be easily accessed by the user. For example, the opening may be 4-5 cm in diameter. The portion of the sleeve surrounding the opening 112 may be reinforced in any appropriate manner such as adding a reinforcing material. Also, means may be provided for securing the tubular entry port of the collection receptacle relative to the opening 112. For example, the support sleeve may include straps 120 having first ends connected to the support sleeve near the opening 112 and some type of connecting band 118 such as an elastic band or flexible metal-based twist tie, while the tubular entry port may have a support ring provided therewith which has an annular groove defined around an outer surface thereof such as the ring 138 with groove 139 in FIGS. 10A, 10C. With such features the tubular entry port may be easily secured relative to the entry port by placing portions of the straps 120 close to their first secured ends against opposite sides of the entry port and then the connecting band 118 may be secured around the straps and into the annular groove 139 of the support ring 138. The straps 120 may be sufficiently long that after portions close to their first ends are connected to the tubular port, the opposite, free ends of the straps may be secured about the user or secured to a garment or belt worn by the user for additionally supporting the support sleeve and the tubular port in desired proximity to the user's genital area. Such additional support may give the user a greater feeling of reliability regarding support of the urinary collection apparatus on the user.

Again referring to FIG. 11B, the large opening 114 on the rear side of the fabric support sleeve may be linear and may extend the full length of the fabric sleeve or may extend less than the full length provided that it is large enough to permit the urine collection apparatus to be easily inserted and removed from the sleeve. The opening 114 may have closure device provided therewith such as a zipper, a hook-and-loop fastener, buttons, etc. For example a plastic zipper such as provided with plastic bags or any other water-tight closure may be used.

The fabric support sleeve 110 may include the waistband 116 and/or some other type of mechanism for securing the sleeve to a user. As depicted, the waistband 116 may be a continuous member formed of an elastic material which can be expanded to comfortably fit around a user's waist, and may have portions secured to opposite ends of the fabric support sleeve, e.g., by being fixed to the ends though sewing, adhesive bonding, etc., or the opposite ends of the fabric support sleeve may have tubular receivers provided therewith through which the waistband 116 may be extended. Alternatively, the waistband 116 may be an elongate strap which may be extended through tubular receivers provided on the ends of the fabric support sleeve, then wrapped around the user's waist and ends of the strap may be tied together. Similarly, the ends of the strap could be long enough to extend over the user's shoulders and fastened to the waistline of a garment worn by the user like suspenders. Alternatively, the strap 116 may be affixed to the fabric support sleeve 110 using fasteners, e.g., snaps, buttons, hook-and-loop fasteners, etc. In some embodiments, the strap may have a fastener for fixing the strap to the user's clothing. For example, the strap fastener may be a clip such as used to connect stockings to a garter belt that may be clipped onto underwear to hold the receptacle in place. Still further, other possible means may be provided for securing the support sleeve 110 on a user, e.g., opposite ends of the fabric support sleeve may be secured to the waistline of the garment by one or more of bonding using a releasable fastener such as a button, a hook, or a hook-and-loop type fastener. The support sleeve 110 may be included as part of a larger garment, e.g., it could be included as the center part of underwear which fully surrounds the user's pelvic area so that the small opening 112 faces the user's genital area and the large opening 114 on the rear side of the fabric support sleeve 110 faces away from the user.

When the support fabric support sleeve 110 is being worn by a user, the opposite ends of the sleeve 110 may be respectively disposed generally near a lower abdomen and the sacral region of the user, while extending from upper portions of the user's thighs from front to back over genital and perineal region, although the exact disposition of the fabric support sleeve will depend on the sleeve's length and on the relative size of the user. Such positioning of the fabric support sleeve relative to the user's body assures ease of use and proper, sufficient support of the urine collection receptacle even when the user is moving, sitting, etc., while not unduly restricting the user's movements or creating any unpleasant or undesirable feeling for the user. The fabric support sleeve 110 also provides a balanced spread of urine volume and weight control, e.g., it may prevent the urine retained in urine collection apparatus—receptacle within the sleeve from sloshing, give the user a natural feeling of wearing ordinary underwear, while distributing the weight of the urine retaining apparatus and any urine contained therein to various portion(s) of the user's body for preventing the contained urine from being concentrated near any given portion of the user's body. Still further, although the weight of the user's body will displace the urine contained by the collection apparatus within the fabric support sleeve when the user sits, the collection receptacle may be formed of stretchable, elastic material such as TPU and the elongate shapes of the fabric support sleeve and of the collection receptacle permit the contained urine to reliably spread to fill portions of the collection receptacle into any slack space in front and back portions of collection receptacle within the sleeve, thus minimizing any fluid pressure applied to the collection receptacle. The fabric support sleeve permits different sizes and shapes of the urine collection receptacle to be contained therein, e.g., it could be a receptacle such as 90 or 100 in FIGS. 8, 9 having a tubular entry port at an intermediate portion of the apparatus, a receptacle such as 130 in FIGS. 10A-10C having a tubular entry port at an end portion thereof, it could be an elongate apparatus which snakes back and forth such as the apparatus shown in FIG. 5, etc. If the urine collection apparatus snakes back and forth the apparatus shown in FIG. 5 it may function like a cushion or sponge to provide a physical comfortableness for the user. The support sleeve 110 also allows the urine collection apparatus to have a bigger volume capacity without creating a visible notice of protrusion. Fabric cloth forming the support sleeve may also reduce heat transfer and dispel feeling of just voided urine.

Backflow Preventing Means

While the tubular entry port included with the collection receptacle according to the various exemplary embodiments of the present invention as disclosed herein may function as a means of preventing backflow of urine back out of the collection apparatus through the entry port as discussed herein, it is possible to include additional means or devices for preventing backflow with any of the embodiments. Referring to FIGS. 12A-12C there is shown an exemplary embodiment of one such backflow preventing device 140 according to the present invention which may, for example, be used together with the urinary collection apparatus 130 shown in FIGS. 10A-10C. FIGS. 12A, 12B are front views showing assembly of the backflow preventing device 140, and FIG. 12C is a top view of the assembled device in FIG. 12B. The backflow preventing device 140 resembles the tubular entry port 134 of the collection apparatus 130 and functions similarly to the entry port 134 for preventing backflow. Essentially, the backflow preventing device 140 provides a second level of backflow prevention. It is possible to include more than one backflow preventing device 140 with a urinary collection apparatus according to the present invention, e.g., the multiple backflow preventing devices may be nested together with the tubular entry port of the collection apparatus and each of the backflow preventing devices provides another level of backflow prevention. However, when multiple backflow preventing devices are used it is probably sufficient for one of the devices to include a constricted opening involving an elastic band 144 or the like as discussed below for engaging against a user's penis.

The backflow preventing device 140 generally includes a main body 142 having an open upper end 143 and a small discharge opening 145 at its lower end, and may be manufactured relatively easily from thin, lightweight plastic materials such as latex, TPU, HDPE, LDPE, and LLDPE, a support ring 148 which may be formed of a rigid or semi-rigid material such as a plastic, rubber or elastomer and the elastic band 144 or other device for forming a constricted opening in the backflow preventing device 140 to receive a user's penis. The main body may have any desired length, but typically will be shorter than the main body of the urinary collection apparatus with which it is to be used, and may have a diameter which is the same or less than that of the main body of the urinary collection apparatus as much of the main body 142 of the backflow preventing device 140 will be disposed within the main body of the urinary collection apparatus which it is used with, e.g., main body 132 of the apparatus 130. Generally the backflow preventing device may appear similar to a condom, but with a small discharge opening at one end and a larger opening at the opposite end. The support ring 148 may have an outer diameter (OD) which is slightly smaller than the ID of the support ring 138 of the urinary collection apparatus. If, for example, the OD of the support ring 148 is slightly smaller than the ID of the support ring 138 the support rings 138, 148 may be securely fitted coaxially together for desirably reducing a degree to which the support rings may project from the urinary collection apparatus, and a portion of the main body 142 which is folded over the support ring 148 will be securely retained between the support rings 138, 148. The elastic band 144 may be formed of rubber, an elastic fabric or other elastic material and will ultimately form an entry port 149 for the backflow preventing device 140 into which a user may insert his penis, and correspondingly should not have too small of an inner diameter (ID) and should not cause any discomfort to the user. The entry port 149 may be positioned slightly above the support ring 148 in the assembled backflow preventing device. Given that the elastic band 144 will apply pressure to the user's penis, it may be formed with a relatively large width and small thickness such as a ribbon, so that the pressure as applied will be spread over a larger area which minimizes any possibility that it would cause discomfort, but will still positively support the penis for preventing any urine from leaking back out through the open end 143.

FIG. 12A shows the backflow preventing device 140 as it is being assembled with the support ring 148 disposed within the main body 142 near the upper opening 143 and the elastic band 144 disposed around the main body at a location between the open upper end 132 and the support ring 148. FIGS. 12B, 12C show the backflow preventing device fully assembled after the upper portion of the main body 142 is folded back over itself so that the upper opening 143 is now below the support ring 148 and the elastic band 144 is disposed between the overlapping portions of the main body 142 above the support ring 148. As shown in FIG. 12C the elastic band 144 forms the entry port 149 for the backflow preventing device 140 by drawing the main body 142 to a smaller size than the ID of the support ring. Again, a user's penis may be inserted into such entry port 149, and the elastic band will draw in the material of the main body against the inserted penis to help maintain the penis in the entry port while the user is discharging urine. Again, the elastic band 144 may be relatively wide with small thickness like a ribbon and should not constrict the entry port 149 to too small of size or with excessive strength. The entry port should surround and engage against user's penis, but without causing any discomfort to the user.

For use, the assembled backflow preventing device 140 may be inserted coaxially into the entry port of the urinary collection apparatus, such as the entry port 134 of the apparatus 130 in FIGS. 10A-10C, with the portion of the main body 142 which is folded over the support ring 138 will be securely retained between the support rings 138, 148. Also, another support ring (not shown) may be inserted or disposed between the support rings 138, 148 to reinforce the secure connection of the folded portion of the main body 142 by the support rings, or such additional support ring may be around the outside diameter of the ring 138 coaxially and the folded portion of the of the main body 142 may be secured between the ring 138 and the additional support ring. In use, the user's urine will initially be discharged into the backflow preventing device 140, then into the tubular entry port 134 of the apparatus 130 and finally into the main body. Due to the presence of the backflow preventing device 140, it is much more difficult for urine to flow out of the urine collection apparatus back through the backflow preventing device 140, as well as through the tubular entry port 134.

Figure 13:
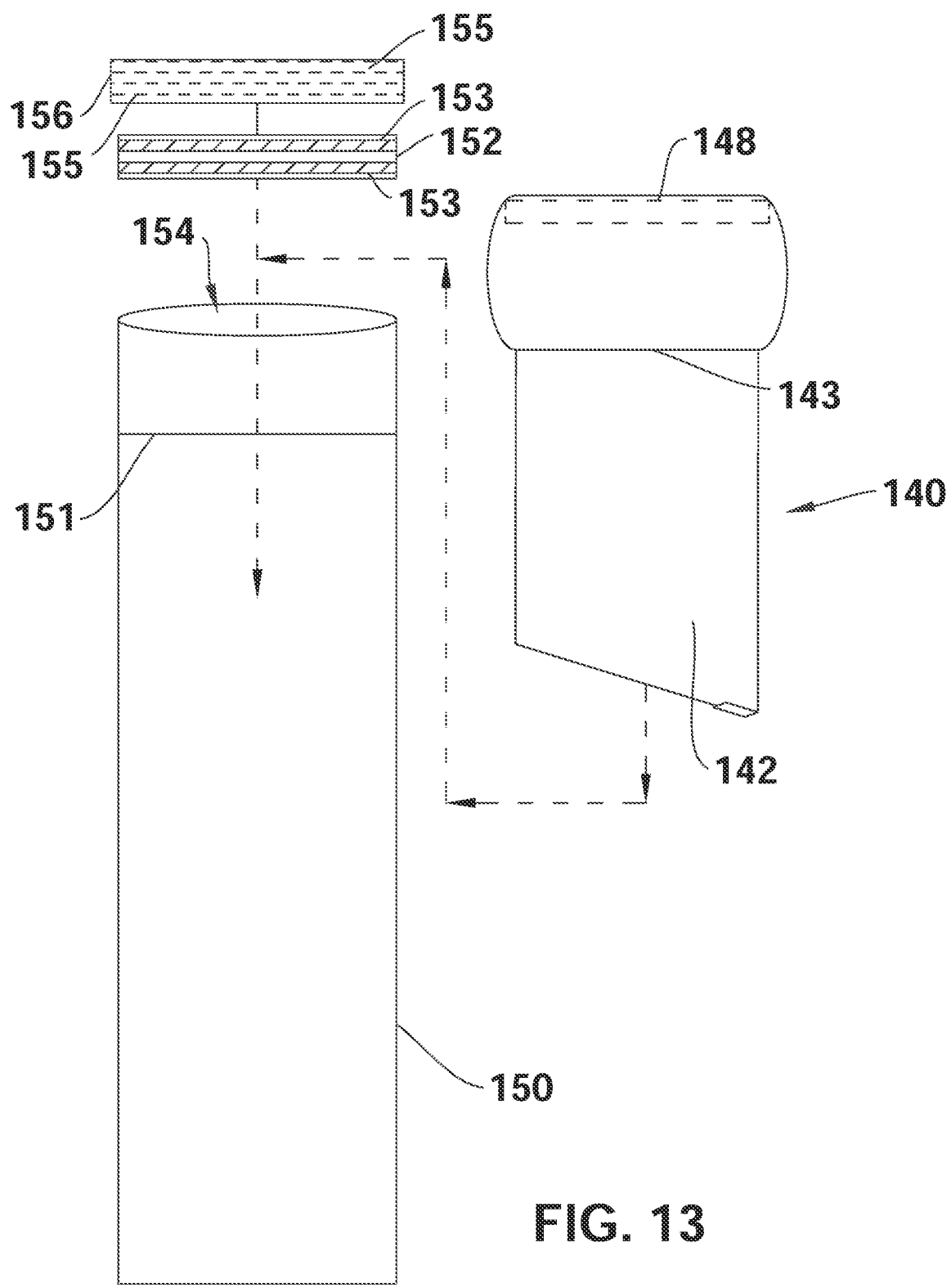
FIG. 13 is an exploded view of another exemplary embodiment of a urinary collection apparatus according to the present invention including a simple elongate receptacle which contains discharged urine, has one closed end and an opposite open end, together with a backflow preventing device such as shown in FIGS. 12A-12C, and two additional rings for connecting the elongate receptacle and the backflow preventing device together.

Urine Collection Receptacle Combined with Backflow Preventing Devices and Other Features Referring to FIG. 13 is shown an exploded view of another exemplary embodiment of a urinary collection apparatus according to the present invention including a simple elongate collection receptacle 150 which contains discharged urine, has one closed end and an opposite open end with an entry port 154, together with the backflow preventing device 140 as shown in FIGS. 12A-12C, and two additional rings 152, 156 for connecting the elongate receptacle and the backflow preventing device together.

The collection receptacle 150 has a very simple structure, e.g., it may an elongate plastic bag formed from thin, lightweight plastic materials such as latex, TPU, HDPE, LDPE, and LLDPE having the open upper end 154 and a closed opposite end, can be made very inexpensively and correspondingly may be considered as disposable. The backflow preventing device 140 may have a structure as disclosed above. The support ring 152 may have an inner diameter which is slightly larger than the outer diameter of the support ring 148, and the support ring 156 may have an inner diameter which is slightly larger than the outer diameter of the support ring 152 such that the three support rings 148, 152, 156 may be securely disposed coaxially together. For assembling this urinary collection apparatus, the backflow preventing device 140 may be inserted into the collection receptacle through the open end 154 such that the upper end of the device 140 including the entry port 149 is disposed slightly down into the receptacle 150 even with the line 151. Next, the support ring 152 is fitted coaxially around the support ring 148 with portions of the main body 142 of the backflow preventing device 140 and the collection receptacle 150 securely fixed between the two support rings 148, 152. Finally, the upper portion of the collection receptacle 150 above the line 151 may be folded over the support ring 152 and then the support ring 156 is fitted coaxially around the support ring 152 with the folded portion of the receptacle 150 securely fixed between the two support rings 152, 156. Indicated at 153 are annular grooves provided on the outer surface of the support ring 152, while indicated at 155 are protruding ridges provided in the inner surface of the support ring 156 which may be fitted into the annular grooves 153 for more reliably connecting the support rings 152, 156 together with the folded portion of the receptacle 150 secured there between.

The urinary collection apparatus of FIG. 13 may be used together with the fabric support sleeve of FIGS. 11A-11B similarly to the collection receptacle of FIGS. 10A-10C, and for such purpose the support ring 156 may also have an annular groove (not shown) provided on its outer surface for use in securing the entry port of the collection apparatus of FIG. 13, including the entry port 149 of the backflow preventing device 140, relative to the smaller opening 112 of the fabric support sleeve using the straps 120 and the connecting band 118.

Figure 14:
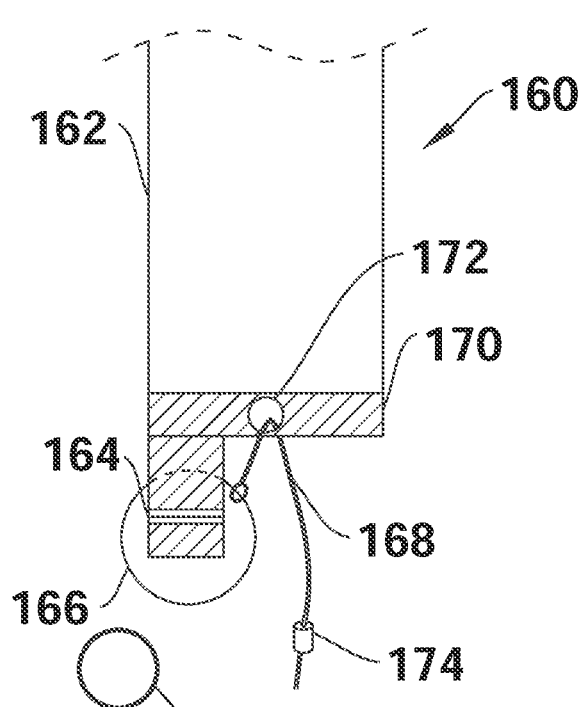
FIG. 14 is a top plan view of a portion of a urine collection receptacle according to the present invention including means for manipulating a discharge opening of the receptacle.

Referring to FIG. 14, there is shown a lower portion of a main body 162 of a urine collection receptacle 160 according to another exemplary embodiment of the present invention. This urine collection receptacle is similar to the urine collection receptacle in some of the other exemplary embodiments of the present invention in that it has a selectively openable/closeable discharge opening 164 provided at a lower end thereof which may be used for emptying out urine that has been received—collected in the receptacle. However, this collection receptacle 160 also includes means for lifting, lowering and otherwise manipulating the lower end of the collection receptacle, as this may be desirable in some situations, e.g., for preventing urine that has collected in the receptacle from leaking out, for positioning the lower end of the receptacle such that it does not interfere with a user's movements or positioning when the user is going to sit or lay down, etc.

As depicted, the lifting and lowering means may include a grip 166 connected to lower end of the collection receptacle near the discharge opening and one or more elongate cords or strings 168 each having one end connected to the grip and an opposite, free end which a user may pull or otherwise manipulate to move the lower end of the collection receptacle including the discharge opening 164 as desired. For example, if the collection receptacle 160 has some urine in it and the user is concerned that he/she may inadvertently sit or lay on the receptacle, which may apply excess pressure that could compromise the integrity of the receptacle and/or causes some of the urine to escape from the receptacle, the user may pull on the string(s) to bring the lower end of the receptacle including the discharge opening 164 to a desired position, e.g., in front of the user's body, at higher level than it would normally be disposed at, etc., so as to avoid undue pressure on the opening 164 and to prevent any leaking or seepage of urine from the receptacle. The opposite, free end of each of the string(s) 168 may be attached to another garment or device worn by the user, e.g., the user's belt, a support harness worn by the user, etc., so that the free end(s) of the string(s) are conveniently located for use and/or to maintain the lower end of the collection receptacle at a desired position. Multiple strings 168 will typically give the user greater control in manipulating and positioning the lower end of the receptacle than a single string.

The lower end of the collection receptacle 162 may include a reinforcement 170 provided therewith, which may be formed using additional layer(s) of the material using in forming the receptacle 160, e.g., TPU, HDPE, LDPE, LLDPE or some other material provided in laminated fashion with the lower end. Also, an opening 172 may be provided through the reinforced lower end and though which the string(s) 168 may be extended for giving additional contact between the string(s) and the lower end of the receptacle. Further, a mechanism 174 for adjusting the effective length of the string may be provided with each of the strings. For example, the mechanism 174 may be a cord-lock type device having an opening through which a looped section of the string may extend, e.g., a user may compress the cord lock with the user's fingers when the user wants to adjust the length of the string and release the cord lock so as to lock the size of the looped section of the string after adjusting the same to a desired size.

The selectively openable/closeable discharge opening 164 at the lower end of the collection receptacle may include various closure mechanisms, e.g., a zip-lock type closure, an elastic band 176 which the user may stretch and extend around a portion of the lower end of the receptacle including the opening 164, and possibly also with the grip 166, for closing the opening and which may be removed to open the opening, a clip which may be selectively applied to and removed from the opening, a combination of these, etc.

Other Flowback Prevention Means

According to another important aspect of the invention, various means may be provided with a urine collection receptacle according to the present invention for assuring that all of the urine being discharged by a user will be safely received in the receptacle without unintended spillage and will remain in the receptacle without seeping or spilling back out of the receptacle as the user discharges urine into the collection receptacle and/or when some amount of urine is contained in the collection receptacle and the user continues to wear the receptacle as the user moves, sits, lies down, etc.

Figure 15A:
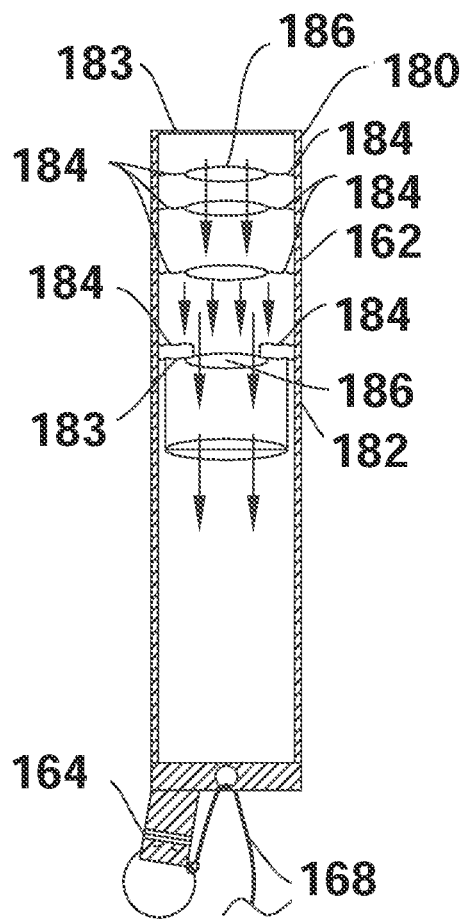
Figure 15B:
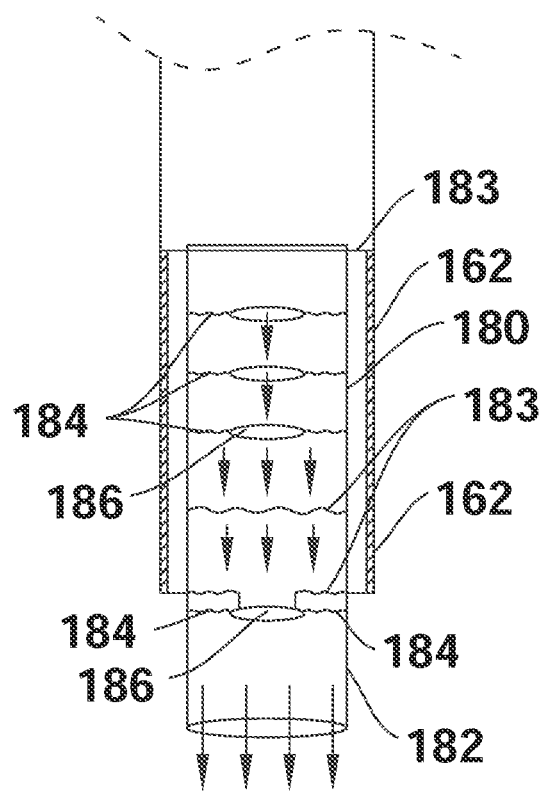

One such means according to an exemplary embodiment of the present invention as shown in FIGS. 15A, 15B is an elongate entrance port or cap 180 that may be provided at the entrance end of a urine collection receptacle according to the present invention for guiding urine discharged by a user into the collection receptacle. Particularly, the cap 180 may include one or more diversions provided along its length that divert or guide flow of urine along a diverted path as the urine is flowing through the entrance cap into the collection receptacle, and which also prevent or minimize the possibility that any of the urine which is flowing into the receptacle or which has been collected in the collection receptacle may undesirably flow back through and out of the entrance cap, rather than remaining in the collection receptacle. FIG. 15A shows the entrance cap 180 provided at an entrance portion of the main body 162 of the collection receptacle 160 discussed above and FIG. 15B shows some details of how these two components may be assembled together.

As shown in FIG. 15A the entrance cap 180 may be provided within an entrance end portion of a main body 162 of the collection receptacle 160 opposite to end of the collection receptacle having the discharge opening 164, and extends into the main body by a predetermined distance, e.g., 10-30 cm. Opposite ends of the entrance cap may be fully open, such that a user's penis may be inserted into one end of the entrance cap so that urine discharged by the user will flow into the entrance cap, through the cap and out the opposite end of the cap into the collection receptacle main body 162. Thus, the cap 180 may form an entry port for the user to insert his penis into the collection receptacle. If desired, a lubricant such as a hydrogel or the like may also be applied to a portion of the user's penis which is inserted into the cap to help prevent undesired flowback and seepage of urine. While this exemplary embodiment has been discussed in relation to a male user having a penis which is inserted into the cap, it will be understood that the various exemplary embodiments of the collection receptacle, the cap, etc. according to the present invention may also be used by female users, and this may involve use of an additional adapter such as shown in FIGS. 3A-3E.

The entrance cap 180 may be formed of the same material(s) used to form the receptacle 160, e.g., thermoplastic urethane (TPU), preferably of ether type, with similar width and wall thickness as those of the collection receptacle 160 as discussed herein such that the cap 180 may be easily inserted into the open end of the receptacle main body 162. For example, the entrance cap 180 may be 6-10 cm in width and 10-30 cm long while laying flat, and may have a wall thickness of 0.0025-0.0075 mm (1-3 mil). As discussed, TPU has several advantageous characteristics which are useful for the collection receptacle and which are also useful for the cap, including that TPU is relatively strong and flexible and unlikely to rupture even if some amount of pressure is applied thereto, sheets or films of TPU may be easily and sealingly bonded together using heat or energy pulses for forming the cap including constrictions and diversions, for connecting the cap to the main body 162, etc., and TPU's elasticity is ideal for assuring that the user's penis will be fluid-tightly engaged by the entrance opening of the cap when inserted therein.

For connecting the entrance cap 180 to the main body 162 of the collection receptacle, the cap may be placed inside of the main body at the end opposite to the discharge opening 164 and then the two components may be bonded together by selectively heating portions of the components to form non-constricting joints between portions of the components, e.g. one non-constricting joint at or near the entry ports of the two components, and one or more additional non-constricting joints along the length of the cap so that the cap cannot move relative to the main body at these joints. Also, some constrictions or seals may be provided which bond walls of the cap together to form constrictions or diversions to urine flow through the cap 180, which help to prevent undesired flowback of urine from the collection receptacle. For example, the entrance cap 180 may include one or more of: a first type of non-constricting, annular joint or seal 183 between adjacent walls of the cap and the main body which joins the two components together but does not constrict the flowpath of urine through the cap, and a second type of constricting joint or seal 184 which joins opposing walls of the cap together to create constrictions or diversions for urine as it flows through the cap and/or effectively reduces the size and changes the shape of the flowpath for urine through the cap at the portions of the cap where the seals 184 are provided. The non-constricting and constricting seals 183, 184 may each be provided in various numbers and in one or more shapes and sizes at various portions along the length of the cap. As shown in the embodiments of FIGS. 15A-16B, at least two of the constrictions formed by the constricting seals are arranged in series such that urine discharged from the penis and flowing through the backflow inhibiting device must pass through such at least two of the constrictions before passing into the receptacle.

As depicted in FIGS. 15A, 15B, one of the seals 183 may be provided at or near the open ends of the cap 180 and main body 162 where a user's penis is to be inserted and another of the seals 183 may be provided close to but spaced from an opposite end of the cap such that inner end portion of the cap which extends further inwardmost of the main body 162 beyond this seal 183 forms a so-called "flap" 182 which is tubular in shape as best shown in FIG. 15B, is generally flat because it is formed of the sheet material and can move to some extent relative to the main body 162 and is particularly helpful for preventing backflow of urine through the cap. The flap 182 need not have any of the joints—seals 184 formed therein to be effective for preventing backflow because the opposing walls of the flap will tend to remain engaged together other than when urine is flowing through the cap into the main body. However, the flap may include one or more of the constricting seals 184 if desired. The inventor has determined that width and length of the flap are important for achieving optimum backflow prevention, while assuring the ability of urine discharged by a user to surely flow through the cap into the main body 162. For example, the inventor has determined that when the cap has a flat width of 8-9 cm and one or more of the diversion—restriction forming seals 184 is provided at approximately the same location as the seal 183 which defines one end of the flap so as to limit the effective diameter of the backflow within the cap at the location of such seal(s) 184 to 2.5-4 cm, a flap length of 4-6 cm will be appropriate for preventing backflow of urine through the cap while permitting urine to surely flow through the cap into the main body 162. If the flap length is shorter than 4 cm it may not surely prevent backflow therethrough. A flap length is more than 6 cm may simply require additional material without providing any better backflow prevention.

The seals 184 may be provided in a wide variety of arrangements so as to create diversions and constrictions of the flowpath through the cap 180, and any of these arrangements may be appropriate for cooperating with the flap 182 to surely prevent backflow while assuring the ability of urine discharged by a user to flow through the cap into the main body 162. For example, in the exemplary embodiment of FIGS. 15A, 15B the seals 184 are provided in opposing pairs, with each pair of seals defining a constricted opening 186 therebetween which has a width which is substantially less than the width of the entrance cap, e.g., the openings 186 may have a flat width of 3-5 cm in comparison to the 6-10 cm flat width of the cap. Any number of pairs of the seals 184 and associated openings 186 may be provided with the cap 180, but through experimentation the inventor has found that 3-4 pairs of the seals 184 and associated openings 186, provided at various portions along the length of the cap and spaced 0.75-1.5 cm apart, is sufficiently effective for preventing flowback of urine through the cap. Also, a user's penis may be extended through one or more of the openings 186 closest to the entrance opening of the cap when discharging urine into the collection receptacle, and this is also helpful for preventing backflow seepage of the urine out of the cap.

FIG. 15B depicts one exemplary manner in which the cap 180 and the main body 162 may be joined together. For connecting the two components, initially the cap 180 may be placed inside the main body 162 of the collection receptacle and the open entrance ends of these components are aligned and joined together with one of the annular joints 183 at their ends, e.g., formed using an impulse type sealer which uses energy or energy pulses to fuse the components together, but does not constrict the internal opening size of the cap. Then the main body 162 may be inverted such that the discharge end thereof is pulled back over the cap such that the cap is exposed, such as shown in FIG. 15B. Then a plurality of the constricting seals 184 may be formed in the cap in any desired arrangement. Finally, the main body may be re-inverted to cover the cap and another annular joint 183 may be formed between the cap and the main body so as to define the flap 182 of the cap which extends further into the main body from the joint 183. Of course, there are other manners in which the cap 180 and the main body 162 may be joined together, e.g. using adhesive, and the seals 184 may be pre-formed in the cap 180 before it is joined to the main body 162, etc.

Figure 16A:
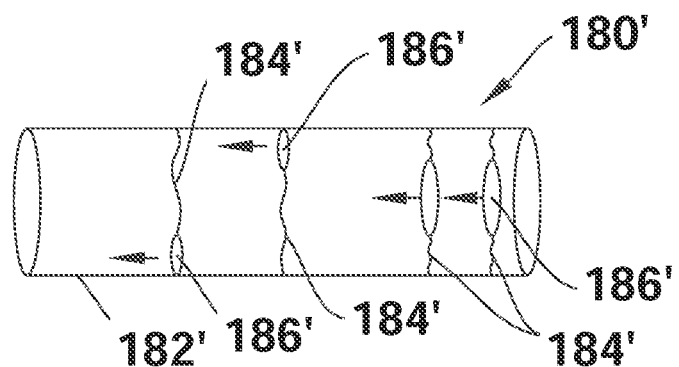
FIGS. 16A, 16B are plan views of other exemplary configuration of an entrance cap similar to the cap in FIGS. 15A, 15B.
Figure 16B:
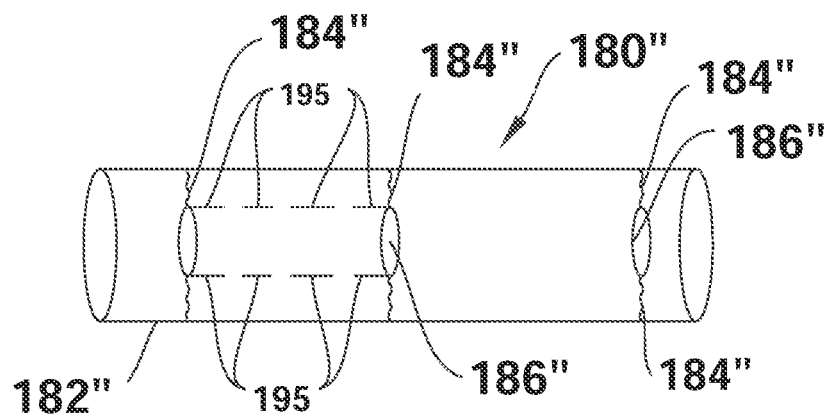

Two other examples of arrangements of seals provided with the cap for creating diversions and restrictions in the flowpath through the cap are shown in FIGS. 16A, 16B. The cap 180' shown in FIG. 16A is very similar to the cap 180 except that some of the diverting—constricting seals 184' are not provided in opposing pairs, but instead are provided individually along the length of the cap and the restricted openings 186' created by such seals 184' are each adjacent to one of the lateral, outer walls of the cap rather than being in the center of the cap when lying flat. The arrangement of the seals 184' in this example is also very effective for preventing flowback of urine from the main body 162 of the receptacle 160, but may cause more restriction on the urine being discharged by a user flowing through the cap into the main body than do the seals 184 in FIG. 15A. The cap 180" shown in FIG. 16B includes a first pair of opposing seals 184" near the cap entrance and two additional pairs of opposing seals 184" spaced away from the entrance, all of which seals 184" may extend transversely of the cap and define associated openings 186" in the center of the cap between opposing pairs of the seals, and further includes seals 195 that may extend axially of the cap with open, unsealed spaces extending axially between adjacent ones of the seals 195 and with some of the seals 195 connecting to inner ends of some of the seals 184", e.g., at right angles, such that pockets are formed on opposite sides of the cap by the seals 184", 195 and into which urine may flow. The seals 195 may be provided in any number and any desired length, but the inventor has found that providing 3-5 of the seals on each side of the cap, with a length of 0.5-1.5 cm for each seal 195 and a correspond space between adjacent ones of the seals is effective for creating proper flowback preventing diversions—restrictions in the cap.

Another exemplary means that may be provided with a urine collection receptacle according to the present invention for assuring that all of the urine being discharged by a user will be safely received in the receptacle without unintended spillage and will remain in the receptacle without seeping or spilling back out of the receptacle is shown in FIGS. 17A, 17B. This means may be in the form of another type of cap 200 formed of soft flexible material such as a highly elastic polymer or polymer foam formed of silicone or other appropriate material which would be provided around a portion of a user's penis which is then extended into an opening of a collection receptacle so as to form a leak-preventing seal between the outer surface of the cap and the inner surface of the collection receptacle. FIG. 17A shows a perspective view of the cap 200 and FIG. 17B shows a cross section of the cap along line B-B in FIG. 17A. As depicted the cap 200 may be generally cylindrical in shape with relatively thick walls of soft elastomeric material, a central opening 202 extending axially therethrough and opposite end surfaces of the cap extending concave inward of the cap. The cap may have any appropriate length, e.g., 2-5 cm and an outer diameter which, when the cap is extended onto a user's penis, will snugly fit in the entrance opening of a collection receptacle for preventing flowback of urine through the entrance opening. The diameter of the central opening 202 may be any appropriate size that will snugly engage the user's penis when the cap is provided on the penis, but without causing any discomfort to the user. For example the opening may have a diameter of 1-2 cm, noting that the highly elastic material of the cap will stretch to increase the size of the opening to fit the penis. If desired a lubricant such as a hydrogel or the like may also be applied to surface(s) of the cap 200 which is inserted into the opening entrance of the collection receptacle to help prevent undesired flowback and seepage of urine.

As best shown in FIG. 17B, the degree of the concave shape of the opposite end surface may be fairly obtuse such that in cross section the two sides of the cap 200 extending from the central opening 202 appear like opposing isosceles triangles. With this shape the cap will only engage a small portion of the user's penis but will provide a much larger surface area for engagement with the inner surface of the entrance opening of the collection receptacle for preventing backflow and seepage.

As shown in FIG. 17B, the cap 200 may also include a baffle 204 provided in association with a discharge end of the central opening 202. The baffle 204 may include flap(s) of a flexible material, e.g., TPU, HDPE, LDPE, LLDPE that extend from the end surface of the cap such that adjacent walls of the flaps will permit urine to flow downward therethrough, but which would otherwise remain engaged together or with the user's penis to prevent flowback of urine.

While the two types of caps 180 and 200 according to the exemplary embodiments of the invention are discussed alternatively for use together with the collection receptacle as flowback preventing means, it is possible to use both types of caps 180, 200 together with the collection receptacle as flowback preventing means.

Figure 19:
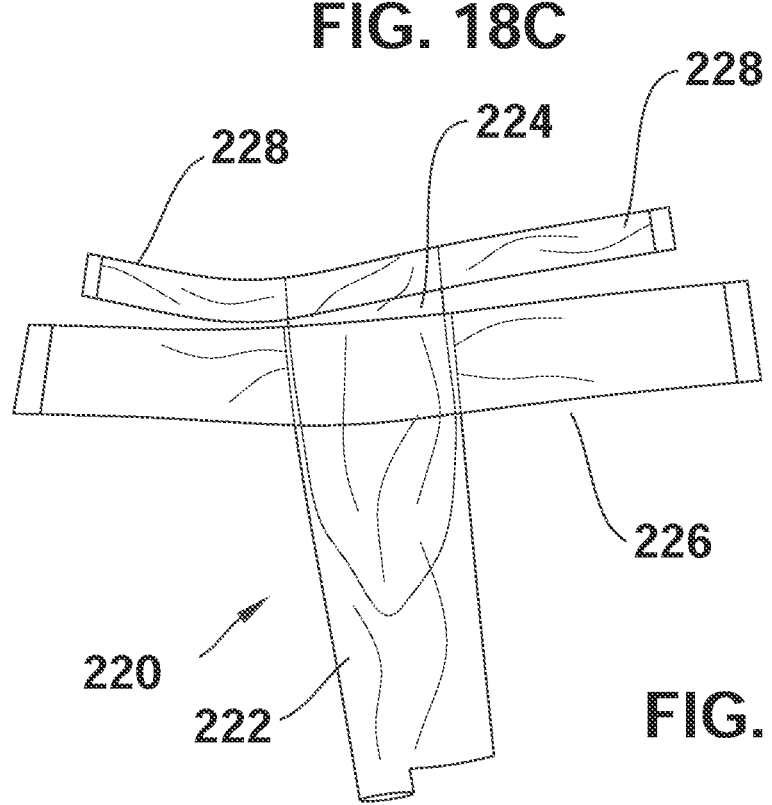
FIG. 19 is a top plan view of a urine collection receptacle according to the present invention which is similar to the receptacle shown in FIGS. 15A, 15B but further includes straps for securing the collection receptacle to the harness shown in FIG. 18A.

FIG. 19 is a perspective view of a collection receptacle 220 according to an exemplary embodiment of the present invention including a main body 222 and an entrance cap 224 provided with the main body at the entrance opening. The main body and the entrance cap respectively include straps 226, 228 provided near their entrance openings which may be used for securing the collection receptacle to a user, e.g., to a harness, a garment, etc. worn by the user, such that the collection receptacle is conveniently located for the user to discharge urine into the entrance opening of the collection receptacle.

Figure 18C:
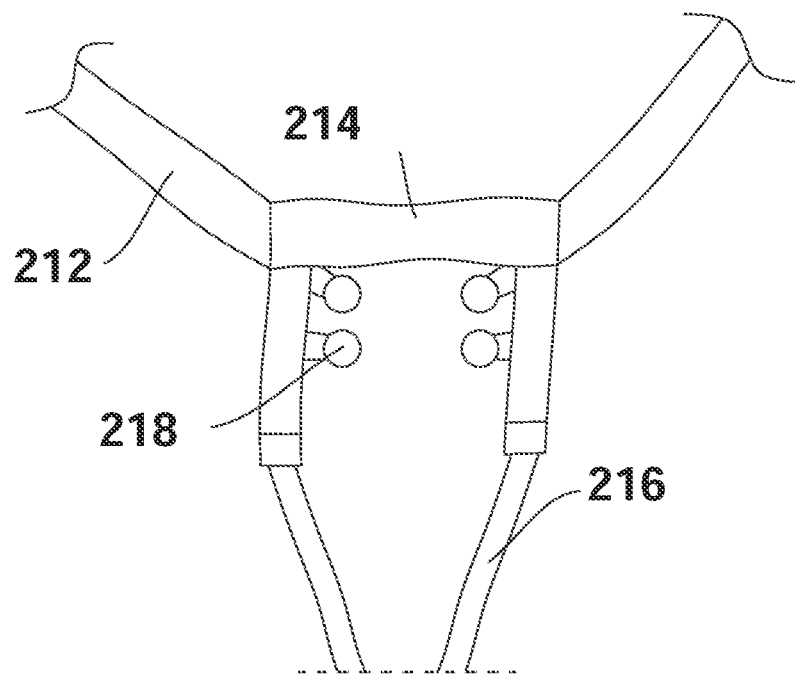
FIG. 18C is an enlarged front view of a portion of the harness of FIG. 18A.

Referring to FIGS. 18A, 18B, 18C there is shown an exemplary embodiment of a harness which may be used to support the collection apparatus on a person, with FIG. 18A showing a perspective view of the harness, FIG. 18B showing manners in which the harness may be worn by a user and FIG. 18C showing an enlarged view of a padded member 214 of the harness of FIG. 18A. Generally, the harness includes an adjustable waist strap 212 which may be secured around a user's waist, a padded member 214 which is configured to extend downward from the waist strap in front of a user's genital area and to have a urine collection receptacle according to the present invention secured thereto, and a pair of securing straps 216, each of which has one end connected to a lower end of the padded member and an opposite free end which may be selectively secured to various portions of the waist strap using an appropriate fastener, e.g., a hook-and-loop type fastener, a clip, a buckle, etc.

The waist strap 212 may be of any appropriate length, may include a fastener associated with free ends of the strap, e.g., a hook-and-loop type fastener, a clip, a buckle, etc., and may include means for adjusting the effective length of the waist strap. The waist strap may be formed of any appropriate material that will not cause any discomfort to the user even if the harness is worn by the user for an extended length of time. For example, it may be made of leather, fabric, elastic material, cushioning material, or a combination of two or more of these.

The padded member 214 may be shaped like an inverted U and provided to extend downward from the waist strap in front of a user's genital area, including a first portion that extends parallel along a portion of the waist strap and a pair of opposing arms that will extend at about right angles to the first portion, and may have a size appropriate for covering the user's genital area, e.g., the first portion may be 8-12 cm long and 2-4 cm wide, and the arms may be 5-7 cm long and 2-4 cm wide. The padded member 214 may be formed of padded or cushioned material(s) that will not cause any discomfort or allergic reaction to a user and may be washed for reuse, e.g., fabric(s), foam covered fabric(s), etc. Also, the padded member may be provided with means 218 for securing a collection receptacle thereto, e.g., loops or hooks which are connected thereto and extend inward of the inverted U shape, such that the entrance opening of the collection receptacle may be conveniently disposed so that a user may readily insert his penis into the entrance opening. Thus, for example, the straps 226, 228 of a collection receptacle 220 including an entrance cap as shown in FIG. 19 may be tied or otherwise secured to the securing means 218, e.g., the collection receptacle 220 and the entrance cap may each include two securing straps 226, 228 disposed near their entrance openings and each of these straps may be separately tied to one of the hoops or hooks forming the securing means 218 so that the entrance openings are disposed directly in front of the user's genital area and such that the user may readily insert his penis into the entrance openings when desired.

The securing straps 216 of the harness may each generally comprise an elongate strip of material having one end secured to an end of one of the arms of the padded member 214 and having a fastener provided on the opposite end of the strap for securing the end of the strap to the waist strap 212, e.g., a hook-and-loop fastener, a clip, a button, etc., and intermediate portions of the straps 216 may be secured together with some type of fastener, e.g., thread which sews the straps together at the intermediate portions, a hook-and-loop fastener, a clip, etc. The material(s) used in forming the straps 216 may be the same as those used for making the waist strap 212 such as discussed above. As depicted in FIG. 19B, the straps may be fastened to the waist strap in various manners depending on the user's preference, e.g., the straps 216 may be arranged to fully overlap with each other and then may be extended between the user's legs adjacent to the user's genital area and having their free ends jointly fastened to the same portion of the waist strap, the free ends of the straps may be extended through the user's legs adjacent to the user's genital area and then separately secured to different portions of the waist strap, etc.

As can be seen from the various embodiments disclosed herein, the present invention provides a urinary collection apparatus including a thin-walled plastic receptacle which is disposable, collapsible, flexible, together with a fabric support sleeve which encloses the receptacle and secures the receptacle in close proximity to the user's genital area, so that the overall apparatus is easy and comfortable to wear and convenient to use for collecting urine when individuals are unable to access a toilet, and is particularly suitable for people who have incontinence. The apparatus is essentially inconspicuous when worn by an individual as it does not project to any significant extent away from the user's body. It is appropriate for use by physically active users. The urinary collection apparatus makes it easy to separate/remove a penis from the receptacle without dislodging other parts of the apparatus. A male user's penis may be pulled out from the urinary receptacle for natural voiding, and similarly a female adapter can be used together with the apparatus so that females may also use the apparatus.

While the present exemplary modes have been described in detail, those familiar with the art will recognize various alternative designs and embodiments within the scope of the following claims. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments discussed herein that are described as less desirable than other embodiments or prior art implementations with respect to one or more characteristics are not outside the scope of the disclosure and may be desirable for particular applications.

For example, while the several exemplary embodiments of the urinary collection receptacle discussed herein are all discussed as being formed of thin, flexible plastic film/sheet material and perhaps also including support rings formed of rigid or semi-rigid materials, the present invention is not limited thereto. It will be understood by persons skilled in the art that an appropriate receptacle may be made with other materials and in other manners, e.g., polymer fabrication—molding of the receptacle integrally including a reinforced tubular entry port but without use of separate support ring(s), the receptacle may be formed with an open end that is reinforced with an elastic material without use of separate support ring(s), etc.

As will be understood, to any extent that some features disclosed in relation to specific exemplary embodiments of the present invention as disclosed herein may also be incorporated into others of the disclosed embodiments, the present invention is intended to cover the same.

For example, the flowback preventing device of FIGS. 12A-12C, 15A-17B may be used together with the tubular entry port of the receptacles according to all of the embodiments, and the fabric support sleeve of FIGS. 11A, 11b may be used with any of the urine collection receptacles according to the invention. As another example, while the urinary collection apparatus 130 in FIGS. 10A-10C and 13 are the only disclosed embodiments having a support ring associated with entry ports thereof, the tubular entry ports of the other embodiments may also include such a support ring. As yet another example, a urine absorbing material, such as used in disposable diapers, may be included with each of the collection receptacles according to the several exemplary embodiments of the invention.

I claim:

1. A wearable urinary collection apparatus for being worn by a user, comprising: an elongate, watertight, flexible receptacle which receives and stores urine therein, including an entrance opening near one end thereof; and an elongate, flexible backflow inhibiting device which is connected to the flexible receptacle, extends within a portion of the flexible receptacle adjacent to the entrance opening of the receptacle and includes an entrance opening near one end thereof, wherein at least one of the entrance opening of the receptacle and the entrance opening of the backflow inhibiting device is configured to receive the user's penis therein such that urine discharged from the penis flows through the backflow inhibiting device into the receptacle, the receptacle and the backflow inhibiting device are each formed of flexible plastic sheet material and are each configured to collapse flat when not in use, and the backflow inhibiting device has constrictions formed therein for constricting and diverting flow of urine therethrough, wherein at least two of the constrictions are arranged in series such that urine discharged from the penis and flowing through the backflow inhibiting device must pass through said at least two of the constrictions before passing into the receptacle, the receptacle and the backflow inhibiting device are connected near their entrance openings and also at an innermost one of the constrictions formed in the backflow inhibiting device, and a lowermost portion of the backflow inhibiting device having a flat tubular flap shape and through which urine is directly discharged from the backflow inhibiting device into the receptacle extends inward of the innermost one of the constrictions by at least 4 cm and is movable relative to the receptacle to help inhibit backflow.

2. The urinary collection apparatus according to claim 1, further comprising a harness which is configured to be selectively attached to the user's body and includes a portion including a padded member shaped like an inverted U which is configured to extend in front of a genital area of the user when the harness is attached to the user's body, wherein at least one of the receptacle and the backflow inhibiting device includes a strap provided near the entrance opening thereof for attaching the at least one of the receptacle and the backflow inhibiting device to the harness portion which is configured to extend in front of the genital area of the user.

3. The urinary collection apparatus according to claim 2, wherein the harness further includes an adjustable waist strap configured to be secured about a waist of the user and a positioning strap having one end connected to the harness portion which is configured to extend from in front of the genital area of the user, between the user's legs to the user's backside, and an opposite, free end which is configured to be selectively attached to the waist strap.

4. The urinary collection apparatus according to claim 1, wherein each of the receptacle and the backflow inhibiting device are formed of thermoplastic urethane (TPU) sheet material and have a wall thickness of 0.0025-0.0075 mm (1-3 mil).

5. The urinary collection apparatus according to claim 1, wherein the receptacle includes a selectively openable and closeable discharge outlet provided near another end thereof opposite to the one end, and the receptacle also includes an elongate cord having one end connected to the other end of the receptacle and an opposite, free end which is configured to manipulated by the user for positioning the other end of the receptacle.

6. The urinary collection apparatus according to claim 1, further comprising an elastic tubular member having an axial center opening configured to be fitted onto the user's penis and having an outer peripheral surface configured to snugly fit within at least one of the entrance opening of the receptacle and the entrance opening of the backflow inhibiting device to minimize any backflow of the urine through said at least one of the entrance opening of the receptacle and the entrance opening of the backflow inhibiting device when the elastic tubular member is fitted onto the user's penis, wherein the elastic tubular member is separate from the receptacle and the backflow inhibiting device and is configured to be separately and removably fitted onto the user's penis apart from the receptacle and the backflow inhibiting device.

7. The urinary collection apparatus according to claim 6, wherein the elastic tubular member is formed of foamed silicone.

8. The urinary collection apparatus according to claim 6, wherein opposite axial ends of the elastic tubular member are concave inward of the elastic tubular member such that an axial length of the center opening is less than an axial length of the elastic tubular member.

9. The urinary collection apparatus according to claim 6, wherein the elastic tubular member includes a baffle provided near one end of the axial center opening formed of flexible plastic sheet material which is configured to engage the user's penis when the elastic tubular member is fitted onto the user's penis.

10. A wearable urinary collection apparatus for being worn by a user, comprising: an elongate, watertight, flexible receptacle which receives and stores urine therein, including an entrance opening near one end thereof; and an elongate, flexible backflow inhibiting device which is connected to the flexible receptacle, extends within a portion of the flexible receptacle adjacent to the entrance opening of the receptacle and includes an entrance opening near one end thereof, wherein at least one of the entrance opening of the receptacle and the entrance opening of the backflow inhibiting device is configured to receive the user's penis therein such that urine discharged from the penis flows through the backflow inhibiting device into the receptacle, the receptacle and the backflow inhibiting device are each formed of flexible plastic sheet material and are each configured to collapse flat when not in use, the backflow inhibiting device has constrictions formed therein for constricting and diverting flow of urine therethrough, at least two of the constrictions are arranged in series such that urine discharged from the penis and flowing through the backflow inhibiting device must pass through said at least two of the constrictions before passing into the receptacle, the receptacle and the backflow inhibiting device are connected near their entrance openings and also at an innermost one of the constrictions formed in the backflow inhibiting device, and the backflow inhibiting device includes an open end portion opposite to the entrance opening thereof which has a flat tubular flap shape, through which urine is directly discharged from the backflow inhibiting device into the receptacle and which is disposed most inward of the receptacle, the open end portion is formed of the flexible plastic sheet material and extends inward of the receptacle beyond an inward most connection between the receptacle and the backflow inhibiting device by at least 4 cm such that open end portion can move relative to the receptacle to help inhibit backflow.

11. A wearable urinary collection apparatus for being worn by a user, comprising: an elongate, watertight, flexible receptacle which receives and stores urine therein, including an entrance opening near one end thereof; and an elongate, flexible backflow inhibiting device which is connected to the flexible receptacle, extends within a portion of the flexible receptacle adjacent to the entrance opening of the receptacle and includes an entrance opening near one end thereof, wherein at least one of the entrance opening of the receptacle and the entrance opening of the backflow inhibiting device is configured to receive the user's penis therein such that urine discharged from the penis flows through the backflow inhibiting device into the receptacle, the receptacle and the backflow inhibiting device are each formed of flexible plastic sheet material and are each configured to collapse flat when not in use, the backflow inhibiting device has constrictions formed therein for constricting and diverting flow of urine therethrough, at least two of the constrictions are arranged in series such that urine discharged from the penis and flowing through the backflow inhibiting device must pass through said at least two of the constrictions before passing into the receptacle, the receptacle and the backflow inhibiting device are connected near their entrance openings and also at an innermost one of the constrictions formed in the backflow inhibiting device, and a lowermost portion of the backflow inhibiting device having a flat tubular flap shape and through which urine is directly discharged from the backflow inhibiting device into the receptacle extends inward of the innermost one of the constrictions by at least 4 cm and is movable relative to the receptacle to help inhibit backflow, wherein the receptacle includes a selectively openable and closeable discharge outlet provided near another end thereof opposite to the one end, and the receptacle also includes an elongate cord having one end connected to the other end of the receptacle and an opposite, free end which is configured to manipulated by the user for positioning the other end of the receptacle.

* * * * *